(12) United States Patent
Short

(10) Patent No.: US 6,489,145 B1
(45) Date of Patent: *Dec. 3, 2002

(54) METHOD OF DNA SHUFFLING

(75) Inventor: Jay M. Short, Encinitas, CA (US)

(73) Assignee: Diversa Corporation, San Diego, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/962,504

(22) Filed: Oct. 31, 1997

Related U.S. Application Data

(63) Continuation-in-part of application No. 08/677,112, filed on Jul. 9, 1996.

(51) Int. Cl.[7] .................................................. C12P 19/34
(52) U.S. Cl. ...................................................... 435/91.1
(58) Field of Search .......................... 435/6, 91.2, 91.1; 536/22.1

(56) References Cited

U.S. PATENT DOCUMENTS

| | | | |
|---|---|---|---|
| 5,605,793 A | 2/1997 | Stemmer | 435/6 |
| 5,672,491 A | 9/1997 | Khosla et al. | 435/148 |
| 5,712,146 A | 1/1998 | Khosla et al. | 435/252.35 |
| 5,811,238 A | 9/1998 | Stemmer et al. | 435/6 |
| 5,830,721 A | 11/1998 | Stemmer et al. | 435/172.1 |
| 5,837,458 A | 11/1998 | Minshull et al. | 435/6 |
| 5,912,119 A | 6/1999 | Radman et al. | 435/6 |
| 5,962,290 A | 10/1999 | Khosla et al. | 435/183 |

FOREIGN PATENT DOCUMENTS

| | | |
|---|---|---|
| WO | WO90/07576 | 7/1990 |
| WO | WO 91/16427 | 10/1991 |
| WO | WO 93/15191 | 8/1993 |
| WO | WO 95/21270 | 8/1995 |
| WO | WO 97/05268 | 2/1997 |
| WO | WO 97/35957 A1 | 10/1997 |

OTHER PUBLICATIONS

Crameri et al., "DNA shuffling of a family of genes from diverse species accelerates directed evolution," Nature 391:288–291 XP000775869 (Jan. 15, 1998).
Database WPI, Section Ch, Week 199644, Derwent Publications Ltd., London, GB; Class B04, AN 1996–43919, XP002141036 & JP 08 217620 A (Meiji Milk Prod Co Ltd) Aug. 27, 1996 (abstract).
Patten et al., "Applications of DNA shuffling to pharmaceuticals and vaccines," Current Opinion in Biotechnology, GB, London 8:724–733, XP002916609.
W. Stemmer, "Rapid evolution of a protein in vitro by DNA shuffling," Nature 370:389–391 (Aug. 4, 1994).
Frohman and Martin, "Detection of Homologous Recombinants," PCR Protocols: A Guide to Methods and Applications, 28:228–236, Academic Press 1990.
Hu and Temin, "Retroviral Recombination and Reverse Transcription," Science 250:1227–1233 (Nov. 30, 1990).
Luo and Taylor, "Template Switching by Reverse Transcriptase during DNA Synthesis," Journal of Virology, 64(9):4321–4328 (Sep. 1990).
Zhang and Temin, "Rate and Mechanism of Nonhomologous Recombination During a Single Cycle of Retroviral Replication," Science, 259:234–238 (Jan. 8, 1993).
Don et al., "'Touchdown' PCR to circumvent spurious priming during gene amplification," Nucleic Acids Research 19(14):4008 (1991).
Bell and DeMarini, "Excessive cycling converts PCR products to random–length higher molecular weight fragments," Nucleic Acids Research, 19(18):5079 (1991).
Jones and Howard, "A Rapid Method for Recombination and Site–Specific Mutagenesis by Placing Homologous Ends on DNA Using Polymerase Chain Reaction," BioTechniques, 10(1):62–66 (1991).
Jones and Winistorfer, "Recombinant Circle PCR and Recombination PCR for Site–Specific Mutagenesis Without PCR Product Purification," BioTechniques, 12(4):528–533.
Stemmer et al., "Rapid evolution of a protein in vitro by DNA shuffling," Nature, Aug. 4, 1994, vol. 370, pp. 389–391.
Patten et al., "Applications of DNA shuffling to pharmaceuticals and vaccines", Current Opinion in Biotechnology, 1997, vol. 8, No. 6, pp. 724–733.
Zhao et al., "Optimization of DNA shuffling for high fidelity recombination", Nucleic Acids Research, Mar. 15, 1997, vol. 25, No. 6, pp. 1307–1308.
Stemmer et al., "DNA shuffling by random fragmentation and reassembly: In vitro recombination for molecular evolution", Proceedings of the National Academy of Sciences, USA, Oct. 1994, vol. 91, pp. 10747–10751.
Smith, G.P., "The progeny of sexual PCT," Nature, Aug. 4, 1994, vol. 374, pp. 324–325.
Crameri et al., "Construction and evolution of antibody–phage libraries by DNA shuffling," Nature Medicine, Jan. 1996, vol. 2, No. 1, pp. 100–102.
Zhao et al., "Functional and nonfunctional mutations distinguished by random recombination of homologous genes," Proceedings of the National Academy of Sciences, USA, Jul. 1997, vol. 94, pp. 7997–8000.
Moore et al., "Strategies for the in vitro evolution of protein function: enzyme evolution by random recombination of improved sequences," Journal of Molecular Biology, 1997, vol. 272, pp. 336–347.

Primary Examiner—Eggerton A. Campbell
(74) Attorney, Agent, or Firm—Gray Cary Ware & Freidenrich LLP; Lisa A. Haile

(57) ABSTRACT

Disclosed is a method of producing random polynucleotides by introducing two or more related polynucleotides into a suitable host cell such that a hybrid polynucleotide is generated by recombination and reductive reassortment. Also provided are vector and expression vehicles including such polynucleotides, polypeptides expressed by the hybrid polynucleotides and a method for screening for hybrid polypeptides.

24 Claims, 7 Drawing Sheets

DNA ADDUCTS

Aristolochic acid 1
Aristolochic acid 2
2-Amino-3-methylimidazo(4,5-f) quinoiline
2-Amino-1-methyl-6-phenylimidazo(4,5-b)pyridine
2-bromoacrolein (2BA)
7-bromomethylbenz(a)anthracene
benzo(a)pyrene
benzo(a)pyrene diolepoxide
Mitomycin C
camptothecin
(+)-CC-1065 (from Streptomyces zelensis)
N-hydroxy-4'-flouro-4acetylaminobiphenyl
trivalent chromium
aromatic amines
platimun(II)
UV

FIG. 4

CREATING DNA ADDUCTS USING U.V. LIGHT

1. IRRADIATE POOL OF TEMPLATE DNA WITH U.V. LIGHT.

5'AGATTAAGGAGTCCGTAAGGATT3'
   5'AGATTAAGGAGTCCGTAAGGATT3'
   5'AGATTAAGGAGTCCGTAAGGATT3'

2. CROSS LINKS IN THE DNA WILL BE INTRODUCED BY THE U.V. THESE CROSS LINKS WILL STOP TAQ POLYMERASE EXTENSION.

5'AGATTAAGGAGTCCGTAAGGATT3'
   5'AGATTAAGGAGTCCGTAAGGATT3'
   5'AGATTAAGGAGTCCGTAAGGATT3'

3. USE RANDOM PRIMERS ON CROSS LINKED DNA AND EXTEND WITH TAQ POLYMERASE

3'AGGCAT5'
   5'AGATTAAGGAGTCCGTAAGGATT3'

3'CCTAA5'
   5'AGATTAAGGAGTCCGTAAGGATT3'

3'CTCAG5'
   5'AGATTAAGGAGTCCGTAAGGATT3'

4. TAQ EXTENSIONS ARE BLOCKED BY U.V. ADDUCTS. THIS CREATES RANDOM SIZE FRAGMENTS READY FOR GENE SHUFFLING

3'TCTAATTCCTCAGGCAT5'
   3'AGGCATTCCTAA5'
   3'AATTCCTCAG5'

FIG. 5

Reassembly of DNA fragments
Edd Lee

NOVEL MOLECULES PRODUCED BY REDUCTIVE RE-ASSORTMENT
1: A deletion between sequence 1 and sequence 2.

R           R

----→--A---/---→------/--C→-------B-----→--------C→--A--------→--------C→.....

The Product - a novel "AC" molecule

--→--A-----C→------B-----→--------C→--A--------→--------C→.....

2: A deletion between sequence 1 and sequence 3.

R              R

----→--A---/---→--------C→------/-B-------→--------C→--A--------→--------C→.....

The Product - a novel "AB" molecule

----→--A----B-----→--------C→--A--------→--------C→.....

3: A deletion between sequence 3 and sequence 4.

R           R

----→--A--------→--------C→-------B--/---→-------/-C→--A--------→--------C→.....

The Product - a novel "BC" molecule

4: How multiple events can produce even more complex re-assortments:
    Step 1

R               R

----→--A---/---→--------C→-----/-B--/---→--------C→--A--------→--------C→.....

The Product - a novel "AB" molecule

----→--A----B----→--------C→--A--------→--------C→.....

Step 2
                      R                      R

----→--A----B--/---→--------C→--A--------→-------/--C→.....

The Product - a novel "ABC" molecule

METHOD OF DNA SHUFFLING

The present application is a continuation-in-part of U.S. patent application Ser. No. 08/677,112 filed on Jul. 9, 1996.

FIELD OF THE INVENTION

This invention relates generally to recombination and more specifically to a method for preparing polynucleotides encoding a polypeptide by a method of in vivo re-assortment of polynucleotide sequences containing regions of partial homology, assembling the polynucleotides to form at least one polynucleotide and screening the polynucleotides for the production of polypeptide(s) having a useful property.

BACKGROUND

An exceedingly large number of possibilities exist for purposeful and random combinations of amino acids within a protein to produce useful hybrid proteins and their corresponding biological molecules encoding for these hybrid proteins, i.e., DNA, RNA. Accordingly, there is a need to produce and screen a wide variety of such hybrid proteins for a useful utility, particularly widely varying random proteins.

The complexity of an active sequence of a biological macromolecule (e.g., proteins, DNA) has been called its information content ("IC"), which has been defined as the resistance of the active protein to amino acid sequence variation (calculated from the minimum number of invariable amino acids (bits) required to describe a family of related sequences with the same function. Proteins that are more sensitive to random mutagenesis have a high information content.

Molecular biology developments, such as molecular libraries, have allowed the identification of quite a large number of variable bases, and even provide ways to select functional sequences from random libraries. In such libraries, most residues can be varied (although typically not all at the same time) depending on compensating changes in the context. Thus, while a 100 amino acid protein can contain only 2,000 different mutations, $20^{100}$ sequence combinations are possible.

Information density is the IC per unit length of a sequence. Active sites of enzymes tend to have a high information density. By contrast, flexible linkers of information in enzymes have a low information density.

Current methods in widespread use for creating alternative proteins in a library format are error-prone polymerase chain reactions and cassette mutagenesis, in which the specific region to be optimized is replaced with a synthetically mutagenized oligonucleotide. In both cases, a substantial number of mutant sites are generated around certain sites in the original sequence.

Error-prone PCR uses low-fidelity polymerization conditions to introduce a low level of point mutations randomly over a long sequence. In a mixture of fragments of unknown sequence, error-prone PCR can be used to mutagenize the mixture. The published error-prone PCR protocols suffer from a low processivity of the polymerase. Therefore, the protocol is unable to result in the random mutagenesis of an average-sized gene. This inability limits the practical application of error-prone PCR. Some computer simulations have suggested that point mutagenesis alone may often be too gradual to allow the large-scale block changes that are required for continued and dramatic sequence evolution. Further, the published error-prone PCR protocols do not allow for amplification of DNA fragments greater than 0.5 to 1.0 kb, limiting their practical application. In addition, repeated cycles of error-prone PCR can lead to an accumulation of neutral mutations with undesired results, such as affecting a protein's immunogenicity but not its binding affinity.

In oligonucleotide-directed mutagenesis, a short sequence is replaced with a synthetically mutagenized oligonucleotide. This approach does not generate combinations of distant mutations and is thus not combinatorial. The limited library size relative to the vast sequence length means that many rounds of selection are unavoidable for protein optimization. Mutagenesis with synthetic oligonucleotides requires sequencing of individual clones after each selection round followed by grouping them into families, arbitrarily choosing a single family, and reducing it to a consensus motif. Such motif is resynthesized and reinserted into a single gene followed by additional selection. This step process constitutes a statistical bottleneck, is labor intensive, and is not practical for many rounds of mutagenesis.

Error-prone PCR and oligonucleotide-directed mutagenesis are thus useful for single cycles of sequence fine tuning, but rapidly become too limiting when they are applied for multiple cycles.

Another limitation of error-prone PCR is that the rate of down-mutations grows with the information content of the sequence. As the information content, library size, and mutagenesis rate increase, the balance of down-mutations to up-mutations will statistically prevent the selection of further improvements (statistical ceiling).

In cassette mutagenesis, a sequence block of a single template is typically replaced by a (partially) randomized sequence. Therefore, the maximum information content that can be obtained is statistically limited by the number of random sequences (i.e., library size). This eliminates other sequence families which are not currently best, but which may have greater long term potential.

Also, mutagenesis with synthetic oligonucleotides requires sequencing of individual clones after each selection round. Thus, such an approach is tedious and impractical for many rounds of mutagenesis.

Thus, error-prone PCR and cassette mutagenesis are best suited, and have been widely used, for fine-tuning areas of comparatively low information content. One apparent exception is the selection of an RNA ligase ribozyme from a random library using many rounds of amplification by error-prone PCR and selection.

In nature, the evolution of most organisms occurs by natural selection and sexual reproduction. Sexual reproduction ensures mixing and combining of the genes in the offspring of the selected individuals. During meiosis, homologous chromosomes from the parents line up with one another and cross-over part way along their length, thus randomly swapping genetic material. Such swapping or shuffling of the DNA allows organisms to evolve more rapidly.

In recombination, because the inserted sequences were of proven utility in a homologous environment, the inserted sequences are likely to still have substantial information content once they are inserted into the new sequence.

The term Applied Molecular Evolution ("AME") means the application of an evolutionary design algorithm to a specific, useful goal. While many different library formats for AME have been reported for polynucleotides, peptides and proteins (phage, lacI and polysomes), none of these formats have provided for recombination by random crossovers to deliberately create a combinatorial library.

Theoretically there are 2,000 different single mutants of a 100 amino acid protein. However, a protein of 100 amino acids has $20^{100}$ possible sequence combinations, a number which is too large to exhaustively explore by conventional methods. It would be advantageous to develop a system which would allow generation and screening of all of these possible combination mutations.

Some workers in the art have utilized an in vivo site specific recombination system to generate hybrids of combine light chain antibody genes with heavy chain antibody genes for expression in a phage system. However, their system relies on specific sites of recombination and is limited accordingly. Simultaneous mutagenesis of antibody CDR regions in single chain antibodies (scFv) by overlapping extension and PCR have been reported.

Others have described a method for generating a large population of multiple hybrids using random in vivo recombination. This method requires the recombination of two different libraries of plasmids, each library having a different selectable marker. The method is limited to a finite number of recombinations equal to the number of selectable markers existing, and produces a concomitant linear increase in the number of marker genes linked to the selected sequence(s).

In vivo recombination between two homologous, but truncated, insect-toxin genes on a plasmid has been reported as a method of producing a hybrid gene. The in vivo recombination of substantially mismatched DNA sequences in a host cell having defective mismatch repair enzymes, resulting in hybrid molecule formation has been reported.

SUMMARY OF THE INVENTION

The method of the present invention utilizes the natural property of cells to recombine molecules and/or to mediate reductive processes that reduce the complexity of sequences and extent of repeated or consecutive sequences possessing regions of homology.

It is an object of the present invention to provide a method for generating hybrid polynucleotides encoding biologically active hybrid polypeptides with enhanced activities. In accomplishing these and other objects, there has been provided, in accordance with one aspect of the invention, a method for introducing polynucleotides into a suitable host cell and growing the host cell under conditions which produce a hybrid polynucleotide.

In another aspect of the invention, the invention provides a method for screening for biologically active hybrid polypeptides encoded by hybrid polynucleotides. The present method allows for the identification of biologically active hybrid polypeptides with enhanced biological activities.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 4 is a list of DNA adducts examples and UV light which may be utilized to halt PCR and generate random polynucleotides.

FIG. 5 is a flow chart illustrates the steps involved in utilizing UV light to create DNA adducts and halt PCR to generate random polynucleotides.

FIG. 6B is directed in its lane one to illustrating separation bands of reassembled polynucleotides after the first round of reassembly PCR and in lane two illustrating separation bands of reassembled polynucleotides after the second round of reassembly PCR. Lane 2 shows the complete, reassembled random polynucleotide ready for amplification, cloning and screening for a useful utility.

FIG. 7 shows a diagram of the production of novel polynucleotides through reductive re-assortment of polynucleotides A, B and C.

DETAILED DESCRIPTION OF THE INVENTION

Figure 1:
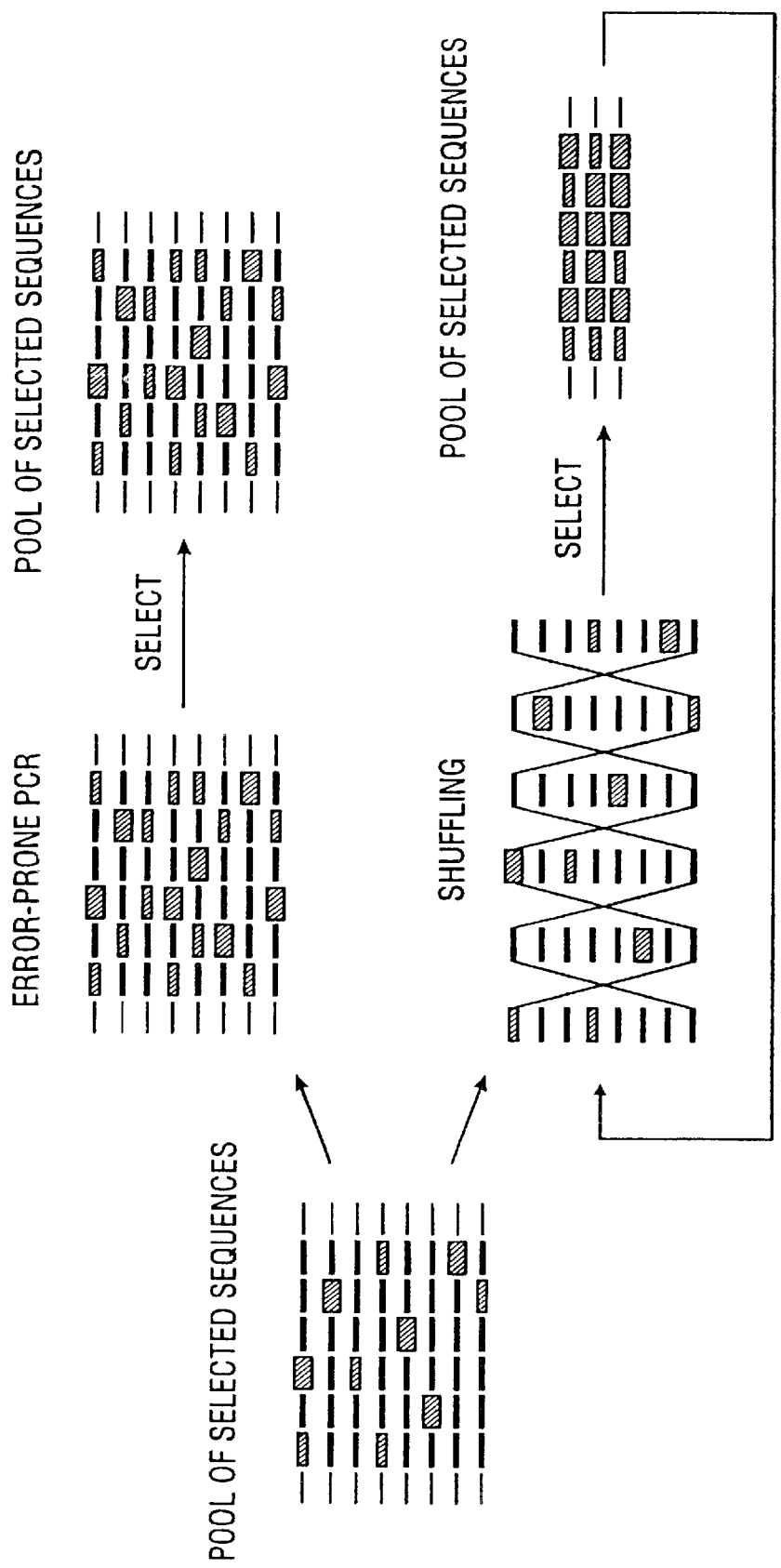
FIG. 1 is a prior art diagram illustrating the resulting hybrid polynucleotide from mutations by error-prone PCR as contrasted with those from shuffling and recombination of shorter or smaller polynucleotides.

The invention described herein is directed to the use of repeated cycles of reductive reassortment, recombination and selection which allow for the directed molecular evolution of highly complex linear-sequences, such as DNA, RNA or proteins thorough recombination.

In vivo shuffling of molecules can be performed utilizing the natural property of cells to recombine multimers. While recombination in vivo has provided the major natural route to molecular diversity, genetic recombination remains a relatively complex process that involves 1) the recognition of homologies; 2) strand cleavage, strand invasion, and metabolic steps leading to the production of recombinant chiasma; and finally 3) the resolution of chiasma into discrete recombined molecules. The formation of the chiasma requires the recognition of homologous sequences.

In a preferred embodiment, the invention relates to a method for producing a hybrid polynucleotide from at least a first polynucleotide and a second polynucleotide. The present invention can be used to produce a hybrid polynucleotide by introducing at least a first polynucleotide and a second polynucleotide which share at least one region of partial sequence homology into a suitable host cell. The regions of partial sequence homology promote processes which result in sequence reorganization producing a hybrid polynucleotide. The term "hybrid polynucleotide", as used herein, is any nucleotide sequence which results from the method of the present invention and contains sequence from at least two original polynucleotide sequences. Such hybrid polynucleotides can result from intermolecular recombination events which promote sequence integration between DNA molecules. In addition, such hybrid polynucleotides can result from intramolecular reductive reassortment processes which utilize repeated sequences to alter a nucleotide sequence within a DNA molecule.

The invention provides a means for generating hybrid polynucleotides which may encode biologically active hybrid polypeptides. In one aspect, the original polynucleotides encode biologically active polypeptides. The method of the invention produces new hybrid polypeptides by utilizing cellular processes which integrate the sequence of the original polynucleotides such that the resulting hybrid polynucleotide encodes a polypeptide demonstrating activities derived from the original biologically active polypeptides. For example, the original polynucleotides may encode a particular enzyme from different microorganisms. An enzyme encoded by a first polynucleotide from one organism may, for example, function effectively under a particular environmental condition, e.g. high salinity. An enzyme encoded by a second polynucleotide from a different organism may function effectively under a different environmental condition, such as extremely high temperatures. A hybrid polynucleotide containing sequences from the first and second original polynucleotides may encode an enzyme which exhibits characteristics of both enzymes encoded by the original polynucleotides. Thus, the enzyme encoded by the hybrid polynucleotide may function effectively under environmental conditions shared by each of the enzymes encoded by the first and second polynucleotides, e.g., high salinity and extreme temperatures.

Enzymes encoded by the original polynucleotides of the invention include, but are not limited to; oxidoreductases, transferases, hydrolases, lyases, isomerases and ligases. A hybrid polypeptide resulting from the method of the invention may exhibit specialized enzyme activity not displayed in the original enzymes. For example, following recombination and/or reductive reassortment of polynucleotides encoding hydrolase activities, the resulting hybrid polypeptide encoded by a hybrid polynucleotide can be screened for specialized hydrolase activities obtained from each of the original enzymes, i.e. the type of bond on which the hydrolase acts and the temperature at which the hydrolase functions. Thus, for example, the hydrolase may be screened to ascertain those chemical functionalities which distinguish the hybrid hydrolase from the original hydrolyases, such as: (a) amide (peptide bonds), i.e. proteases; (b) ester bonds, i.e. esterases and lipases; (c) acetals, i.e., glycosidases and, for example, the temperature, pH or salt concentration at which the hybrid polypeptide functions.

Sources of the original polynucleotides may be isolated from individual organisms ("isolates"), collections of organisms that have been grown in defined media ("enrichment cultures"), or, most preferably, uncultivated organisms ("environmental samples"). The use of a culture-independent approach to derive polynucleotides encoding novel bioactivities from environmental samples is most preferable since it allows one to access untapped resources of biodiversity.

"Environmental libraries" are generated from environmental samples and represent the collective genomes of naturally occurring organisms archived in cloning vectors that can be propagated in suitable prokaryotic hosts. Because the cloned DNA is initially extracted directly from environmental samples, the libraries are not limited to the small fraction of prokaryotes that can be grown in pure culture. Additionally, a normalization of the environmental DNA present in these samples could allow more equal representation of the DNA from all of the species present in the original sample. This can dramatically increase the efficiency of finding interesting genes from minor constituents of the sample which may be under-represented by several orders of magnitude compared to the dominant species.

For example, gene libraries generated from one or more uncultivated microorganisms are screened for an activity of interest. Potential pathways encoding bioactive molecules of interest are first captured in prokaryotic cells in the form of gene expression libraries. Polynucleotides encoding activities of interest are isolated from such libraries and introduced into a host cell. The host cell is grown under conditions which promote recombination and/or reductive reassortment creating potentially active biomolecules with novel or enhanced activities.

The microorganisms from which the polynucleotide may be prepared include prokaryotic microorganisms, such as Eubacteria and Archaebacteria, and lower eukaryotic microorganisms such as fungi, some algae and protozoa. Polynucleotides may be isolated from environmental samples in which case the nucleic acid may be recovered without culturing of an organism or recovered from one or more cultured organisms. In one aspect, such microorganisms may be extremophiles, such as hyperthermophiles, psychrophiles, psychrotrophs, halophiles, barophiles and acidophiles. Polynucleotides encoding enzymes isolated from extremophilic microorganisms are particularly preferred. Such enzymes may function at temperatures above 100° C. in terrestrial hot springs and deep sea thermal vents, at temperatures below 0° C. in arctic waters, in the saturated salt environment of the Dead Sea, at pH values around 0 in coal deposits and geothermal sulfur-rich springs, or at pH values greater than 11 in sewage sludge. For example, several esterases and lipases cloned and expressed from extremophilic organisms show high activity throughout a wide range of temperatures and pHs.

Polynucleotides selected and isolated as hereinabove described are introduced into a suitable host cell. A suitable host cell is any cell which is capable of promoting recombination and/or reductive reassortment. The selected polynucleotides are preferably already in a vector which includes appropriate control sequences. The host cell can be a higher eukaryotic cell, such as a mammalian cell, or a lower eukaryotic cell, such as a yeast cell, or preferably, the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

As representative examples of appropriate hosts, there may be mentioned: bacterial cells, such as *E. coli*, Streptonyces, *Salmonella typhimurium*; fungal cells, such as yeast; insect cells such as Drosophila S2 and Spodoptera Sf9; animal cells such as CHO, COS or Bowes melanoma; adenoviruses; and plant cells. The selection of an appropriate host is deemed to be within the scope of those skilled in the art from the teachings herein.

With particular references to various mammalian cell culture systems that can be employed to express recombinant protein, examples of mammalian expression systems include the COS-7 lines of monkey kidney fibroblasts, described by Gluzman, Cell, 23:175(1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

Host cells containing the polynucleotides of interest can be cultured in conventional nutrient media modified as appropriate for activating promoters, selecting transformants or amplifying genes. The culture conditions, such as temperature, pH and the like, are those previously used with the host cell selected for expression, and will be apparent to the ordinarily skilled artisan. The clones which are identified as having the specified enzyme activity may then be sequenced to identify the polynucleotide sequence encoding an enzyme having the enhanced activity.

In another aspect, it is envisioned the method of the present invention can be used to generate novel polynucleotides encoding biochemical pathways from one or more operons or gene clusters or portions thereof. For example, bacteria and many eukaryotes have a coordinated mechanism for regulating genes whose products are involved in related processes. The genes are clustered, in structures referred to as "gene clusters," on a single chromosome and are transcribed together under the control of a single regulatory sequence, including a single promoter which initiates transcription of the entire cluster. Thus, a gene cluster is a group of adjacent genes that are either identical or related, usually as to their function. An example of a biochemical pathway encoded by gene clusters are polyketides. Polyketides are molecules which are an extremely rich source of bioactivities, including antibiotics (such as tetracyclines and erythromycin), anti-cancer agents (daunomycin), immunosuppressants (FK506 and rapamycin), and veterinary products (monensin). Many polyketides (produced by polyketide synthases) are valuable as therapeutic agents. Polyketide synthases are multifunctional enzymes that catalyze the biosynthesis of an enormous variety of carbon chains differing in length and patterns of functionality and cyclization. Polyketide synthase genes fall into gene clusters and at least one type (designated type I) of polyketide synthases have large size genes and enzymes, complicating genetic manipulation and in vitro studies of these genes/proteins.

The ability to select and combine desired components from a library of polyketides, or fragments thereof, and postpolyketide biosynthesis genes for generation of novel polyketides for study is appealing. The method of the present invention makes it possible to facilitate the production of novel polyketide synthases through intermolecular recombination.

Preferably, gene cluster DNA can be isolated from different organisms and ligated into vectors, particularly vectors containing expression regulatory sequences which can control and regulate the production of a detectable protein or protein-related array activity from the ligated gene clusters. Use of vectors which have an exceptionally large capacity for exogenous DNA introduction are particularly appropriate for use with such gene clusters and are described by way of example herein to include the f-factor (or fertility factor) of *E. coli*. This f-factor of *E. coli* is a plasmid which affect high-frequency transfer of itself during conjugation and is ideal to achieve and stably propagate large DNA fragments, such as gene clusters from mixed microbial samples. Once ligated into an appropriate vector, two or more vectors containing different polyketide synthase gene clusters can be introduced into a suitable host cell. Regions of partial sequence homology shared by the gene clusters will promote processes which result in sequence reorganization resulting in a hybrid gene cluster. The novel hybrid gene cluster can then be screened for enhanced activities not found in the original gene clusters.

Therefore, in a preferred embodiment, the present invention relates to a method for producing a biologically active hybrid polypeptide and screening such a polypeptide for enhanced activity by:

introducing at least a first polynucleotide in operable linkage and a second polynucleotide in operable linkage, said at least first polynucleotide and second polynucleotide sharing at least one region of partial sequence homology, into a suitable host cell;

growing the host cell under conditions which promote sequence reorganization resulting in a hybrid polynucleotide in operable linkage;

expressing a hybrid polypeptide encoded by the hybrid polynucleotide;

screening the hybrid polypeptide under conditions which promote identification of enhanced biological activity; and isolating the a polynucleotide encoding the hybrid polypeptide.

Methods for screening for various enzyme activities are known to those of skill in the art and discussed throughout the present specification. Such methods may be employed when isolating the polypeptides and polynucleotides of the present invention.

The term "isolated" means that material is removed from its original environment (e.g., the natural environment if it is naturally occurring). For example, a naturally-occurring polynucleotide or polypeptide present in a living animal is not isolated, but the same polynucleotide or polypeptide separated from some or all of the coexisting materials in the natural system, is isolated.

As used herein, the term "operably linked" refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame.

As representative examples of expression vectors which may be used there may be mentioned viral particles, baculovirus, phage, plasmids, phagemids, cosmids, fosmids, bacterial artificial chromosomes, viral DNA (e.g. vaccinia, adenovirus, foul pox virus, pseudorabies and derivatives of SV40), P1-based artificial chromosomes, yeast plasmids, yeast artificial chromosomes, and any other vectors specific for specific hosts of interest (such as bacillus, aspergillus and yeast) Thus, for example, the DNA may be included in any one of a variety of expression vectors for expressing a polypeptide. Such vectors include chromosomal, nonchromosomal and synthetic DNA sequences. Large numbers of suitable vectors are known to those of skill in the art, and are commercially available. The following vectors are provided by way of example; Bacterial: pQE vectors (Qiagen), pBluescript plasmids, pNH vectors, (lambda-ZAP vectors (Stratagene); ptrc99a, pKK223-3, pDR540, pRIT2T (Pharmacia); Eukaryotic: pXT1, pSG5 (Stratagene), pSVK3, pBPV, pMSG, pSVLSV40 (Pharmacia). However, any other plasmid or other vector may be used as long as they are replicable and viable in the host. Low copy number or high copy number vectors may be employed with the present invention.

A preferred type of vector for use in the present invention contains an f-factor origin replication. The f-factor (or fertility factor) in *E. coli* is a plasmid which effects high frequency transfer of itself during conjugation and less frequent transfer of the bacterial chromosome itself. A particularly preferred embodiment is to use cloning vectors, referred to as "fosmids" or bacterial artificial chromosome (BAC) vectors. These are derived from *E. coli* f-factor which is able to stably integrate large segments of genomic DNA. When integrated with DNA from a mixed uncultured environmental sample, this makes it possible to achieve large genomic fragments in the form of a stable "environmental DNA library."

Another preferred type of vector for use in the present invention is a cosmid vector. Cosmid vectors were originally designed to clone and propagate large segments of genomic DNA. Cloning into cosmid vectors is described in detail in Sambrook, et al., Molecular Cloning A Laboratory Manual, Second Edition, Cold Spring Harbor Laboratory Press, 1989.

The DNA sequence in the expression vector is operatively linked to an appropriate expression control sequence(s) (promoter) to direct RNA synthesis. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. The expression vector also contains a ribosome binding site for translation initiation and a transcription terminator. The vector may also include appropriate sequences for amplifying expression. Promoter regions can be selected from any desired gene using CAT (chloramphenicol transferase) vectors or other vectors with selectable markers.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium.

The cloning strategy permits expression via both vector driven and endogenous promoters; vector promotion may be important with expression of genes whose endogenous promoter will not function in *E. coli*.

The DNA isolated or derived from microorganisms can preferably be inserted into a vector or a plasmid prior to probing for selected DNA. Such vectors or plasmids are preferably those containing expression regulatory sequences, including promoters, enhancers and the like. Such polynucleotides can be part of a vector and/or a composition and still be isolated, in that such vector or composition is not part of its natural environment. Particularly preferred phage or plasmid and methods for introduction and packaging into them are described in detail in the protocol set forth herein.

The selection of the cloning vector depends upon the approach taken, for example, the vector can be any cloning vector with an adequate capacity for multiply repeated copies of a sequence, or multiple sequences that can be successfully transformed and selected in a host cell. One example of such a vector is described in "Polycos vectors: a system for packaging filamentous phage and phagemid vectors using lambda phage packaging extracts", Alting-Mecs MA, Short JM, Gene, Dec. 27, 1993 137:1, 93–100. Propagation/maintenance can be by an antibiotic resistance carried by the cloning vector. After a period of growth, the naturally abbreviated molecules are recovered and identified by size fractionation on a gel or column, or amplified directly. The cloning vector utilized may contain a selectable gene that is disrupted by the insertion of the lengthy construct. As reductive reassortment progresses, the number of repeated units is reduced and the interrupted gene is again expressed and hence selection for the processed construct can be applied. The vector may be an expression/selection vector which will allow for the selection of an expressed product possessing desirable biologically properties. The insert may be positioned downstream of a functional promotor and the desirable property screened by appropriate means.

In vivo reassortment is focused on "inter-molecular" processes collectively referred to as "recombination" which in bacteria, is generally viewed as a "RecA-dependent" phenomenon. The present invention can rely on recombination processes of a host cell to recombine and re-assort sequences, or the cells ability to mediate reductive processes to decrease the complexity of quasi-repeated sequences in the cell by deletion. This process of "reductive reassortment" occurs by an "intra-molecular", RecA-independent process.

Therefore, in another aspect of the present invention, novel polynucleotides can be generated by the process of reductive reassortment. The method involves the generation of constructs containing consecutive sequences (original encoding sequences), their insertion into an appropriate vector, and their subsequent introduction into an appropriate host cell. The reassortment of the individual molecular identities occurs by combinatorial processes between the consecutive sequences in the construct possessing regions of homology, or between quasi-repeated units. The reassortment process recombines and/or reduces the complexity and extent of the repeated sequences, and results in the production of novel molecular species. Various treatments may be applied to enhance the rate of reassortment. These could include treatment with ultra-violet light, or DNA damaging chemicals, and/or the use of host cell lines displaying enhanced levels of "genetic instability". Thus the reassortment process may involve homologous recombination or the natural property of quasi-repeated sequences to direct their own evolution.

Repeated or "quasi-repeated" sequences play a role in genetic instability. In the present invention, "quasi-repeats" are repeats that are not restricted to their original unit structure. Quasi-repeated units can be presented as an array of sequences in a construct; consecutive units of similar sequences. Once ligated, the junctions between the consecutive sequences become essentially invisible and the quasi-repetitive nature of the resulting construct is now continuous at the molecular level. The deletion process the cell performs to reduce the complexity of the resulting construct operates between the quasi-repeated sequences. The quasi-repeated units provide a practically limitless repertoire of templates upon which slippage events can occur. The constructs containing the quasi-repeats thus effectively provide sufficient molecular elasticity that deletion (and potentially insertion) events can occur virtually anywhere within the quasi-repetitive units.

When the quasi-repeated sequences are all ligated in the same orientation, for instance head to tail or vice versa, the cell cannot distinguish individual units. Consequently, the reductive process can occur throughout the sequences. In contrast, when for example, the units are presented head to head, rather than head to tail, the inversion delineates the endpoints of the adjacent unit so that deletion formation will favor the loss of discrete units. Thus, it is preferable with the present method that the sequences are in the same orientation. Random orientation of quasi-repeated sequences will result in the loss of reassortment efficiency, while consistent orientation of the sequences will offer the highest efficiency. However, while having fewer of the contiguous sequences in the same orientation decreases the efficiency, it may still provide sufficient elasticity for the effective recovery of novel molecules. Constructs can be made with the quasi-repeated sequences in the same orientation to allow higher efficiency.

Sequences can be assembled in a head to tail orientation using any of a variety of methods, including the following:

a) Primers that include a poly-A head and poly-T tail which when made single-stranded would provide orientation can be utilized. This is accomplished by having the first few bases of the primers made from RNA and hence easily removed RNAseH.

b) Primers that include unique restriction cleavage sites can be utilized. Multiple sites, a battery of unique sequences, and repeated synthesis and ligation steps would be required.

c) The inner few bases of the primer could be thiolated and an exonuclease used to produce properly tailed molecules.

The recovery of the re-assorted sequences relies on the identification of cloning vectors with a reduced RI. The re-assorted encoding sequences can then be recovered by amplification. The products are re-cloned and expressed. The recovery of cloning vectors with reduced RI can be effected by:

1) The use of vectors only stably maintained when the construct is reduced in complexity.

2) The physical recovery of shortened vectors by physical procedures. In this case, the cloning vector would be recovered using standard plasmid isolation procedures and size fractionated on either an agarose gel, or column with a low molecular weight cut off utilizing standard procedures.

3) The recovery of vectors containing interrupted genes which can be selected when insert size decreases.

4) The use of direct selection techniques with an expression vector and the appropriate selection.

Encoding sequences (for example, genes) from related organisms may demonstrate a high degree of homology and encode quite diverse protein products. These types of sequences are particularly useful in the present invention as quasi-repeats. However, while the examples illustrated below demonstrate the reassortment of nearly identical original encoding sequences (quasi-repeats), this process is not limited to such nearly identical repeats.

Figure 2:
FIG. 2 is a flow chart which illustrates the principles of Sexual PCR in three basic steps: (1) selecting hybrids for generation of random sized polynucleotides of polynucleotides, (2) generating random-sized polynucleotides by halting the PCR process, and reassembling the random-sized polynucleotides via PCR to form random polynucleotides.
Figure 3:
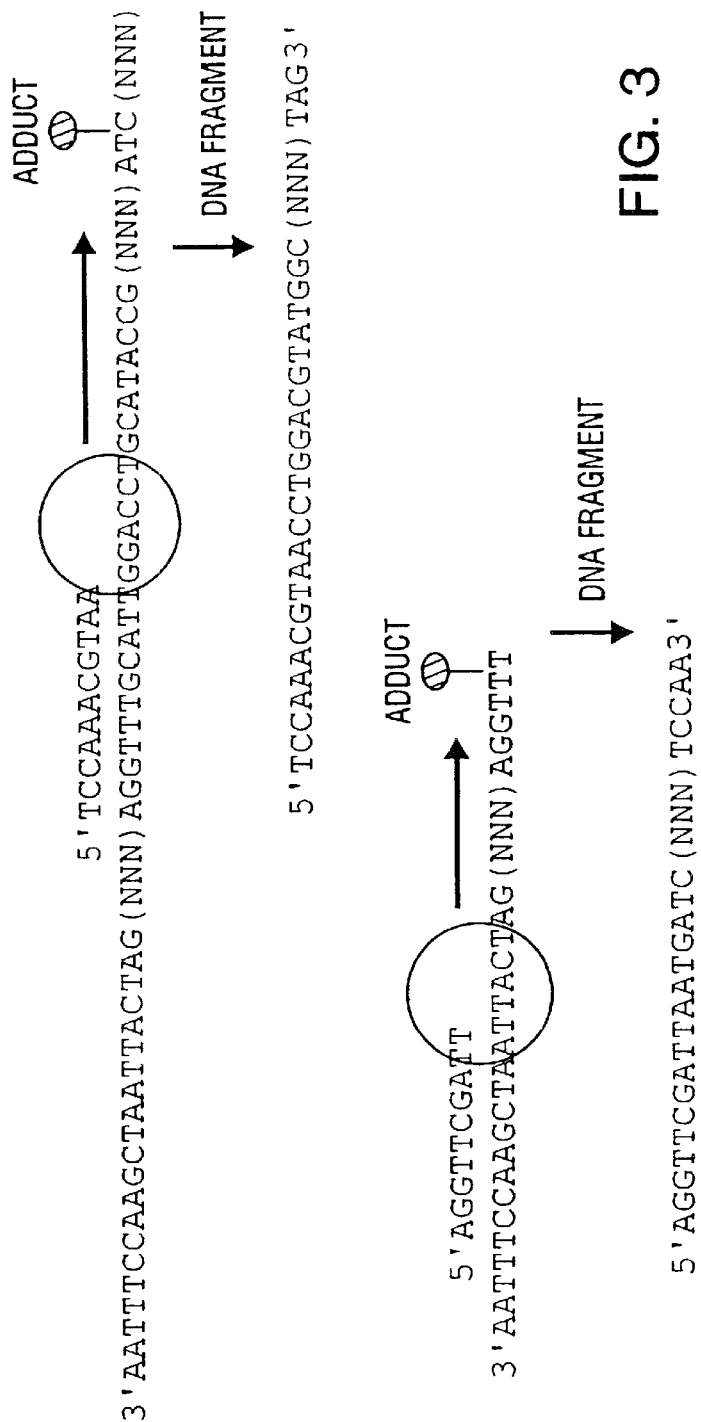
FIG. 3 is a flow chart which illustrates the concepts of utilizing DNA adducts or UV light to halt PCR and to generate random polynucleotides due to random priming and incomplete extension of the strands.
Figure 6A:
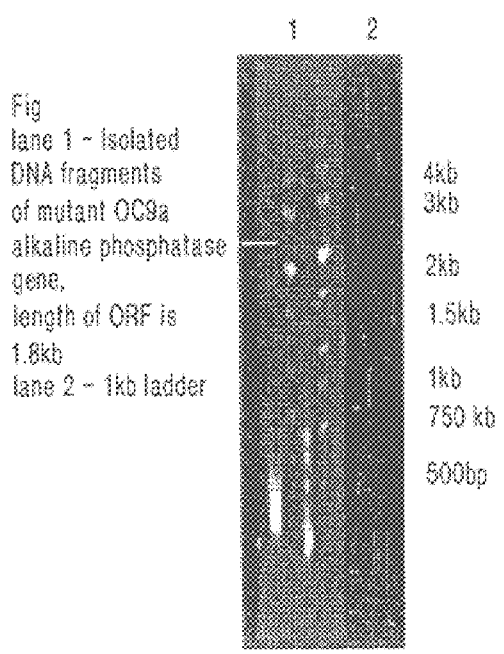
FIG. 6A illustrates the separation bands of the pre-assembly polynucleotides.
Figure 6B:
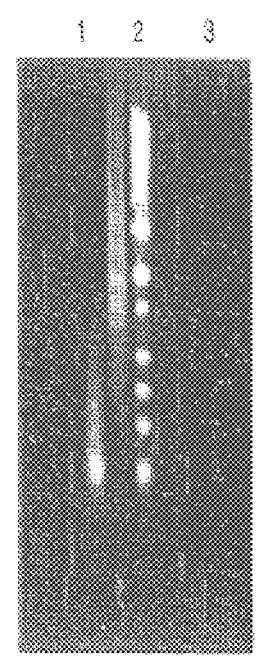
FIG. 6B illustrates the results after polynucleotide assembly.

The following example demonstrates the method of the invention. Encoding nucleic acid sequences (quasi-repeats) derived from three (3) unique species are depicted. Each sequence encodes a protein with a distinct set of properties. Each of the sequences differs by a single or a few base pairs at a unique position in the sequence which are designated "A", "B" and "C". The quasi-repeated sequences are separately or collectively amplified and ligated into random assemblies such that all possible permutations and combinations are available in the population of ligated molecules. The number of quasi-repeat units can be controlled by the assembly conditions. The average number of quasi-repeated units in a construct is defined as the repetitive index (RI). FIG. 2 illustrates an example of an assembled construct.

The following diagram shows a sample set of encoding sequences (quasi-repeats). In this diagram the sequences are represented as three distinct species, each having a unique sequence difference (mutation or variant) labeled "A", "B" and "C".

| DESCRIPTION OF THE CODING UNITS | | |
|---|---|---|
| ENCODING UNIT I | ENCODING UNIT II | ENCODING UNIT III |
| o-A - - - → | o - - - B - - - → | o - - - C - - - → |

The following diagram is an example of an assembled construct containing a random assortment of the three unique encoding sequences represented in the previous diagram. The length of the construct and the number of encoding units is controlled during assembly and can be adjusted to the individual experimental needs.

| ASSEMBLY OF CONCATOMERS |
|---|
| - - - → - - - A - - - → - - - B - - - →C→ - - - A - - - → - - - C→ . . . |

Once formed, the constructs may, or may not be size fractionated on an agarose gel according to published protocols, inserted into a cloning vector, and transfected into an appropriate host cell. The cells are then propagated and "reductive reassortment" is effected. The rate of the reductive reassortment process may be stimulated by the introduction of DNA damage if desired. Whether the reduction in RI is mediated by deletion formation between repeated sequences by an "intra-molecular" mechanism, or mediated by recombination-like events through "inter-molecular" mechanisms is immaterial. The end result is a reassortment of the molecules into all possible combinations as illustrated in FIG. 7.

Optionally, the method comprises the additional step of screening the library members of the shuffled pool to identify individual shuffled library members having the ability to bind or otherwise interact (e.g., such as catalytic antibodies) with a predetermined macromolecule, such as for example a proteinaceous receptor, peptide oligosaccharide, viron, or other predetermined compound or structure.

The displayed polypeptides, antibodies, peptidomimetic antibodies, and variable region sequences that are identified from such libraries can be used for therapeutic, diagnostic, research and related purposes (e.g., catalysts, solutes for increasing osmolarity of an aqueous solution, and the like), and/or can be subjected to one or more additional cycles of shuffling and/or affinity selection. The method can be modified such that the step of selecting for a phenotypic characteristic can be other than of binding affinity for a predetermined molecule (e.g., for catalytic activity, stability oxidation resistance, drug resistance, or detectable phenotype conferred upon a host cell).

The present invention provides a method for generating libraries of displayed antibodies suitable for affinity interactions screening. The method comprises (1) obtaining first a plurality of selected library members comprising a displayed antibody and an associated polynucleotide encoding said displayed antibody, and obtaining said associated polynucleotide encoding for said displayed antibody and obtaining said associated polynucleotides or copies thereof, wherein said associated polynucleotides comprise a region of substantially identical variable region framework sequence, and (2) introducing said polynucleotides into a suitable host cell and growing the cells under conditions which promote recombination and reductive reassortment resulting in shuffled polynucleotides. CDR combinations comprised by the shuffled pool are not present in the first plurality of selected library members, said shuffled pool composing a library of displayed antibodies comprising CDR permutations and suitable for affinity interaction screening. Optionally, the shuffled pool is subjected to affinity screening to select shuffled library members which bind to a predetermined epitope (antigen) and thereby selecting a plurality of selected shuffled library members. Further, the plurality of selectively shuffled library members can be shuffled and screened iteratively, from 1 to about 1000 cycles or as desired until library members having a desired binding affinity are obtained.

In another aspect of the invention, it is envisioned that prior to or during recombination or reassortment, polynucleotides generated by the method of the present invention can be subjected to agents or processes which promote the introduction of mutations into the original polynucleotides. The introduction of such mutations would increase the diversity of resulting hybrid polynucleotides and polypeptides encoded therefrom. The agents or processes which promote mutagenesis can include, but are not limited to: (+)-CC-1065, or a synthetic analog such as (+)-CC-1065-(N3-Adenine), (see. Biochem. 31, 2822–2829 (1992)); a N-acelylated or deacetylated 4'-fluro-4-aminobiphenyl adduct capable of inhibiting DNA synthesis (see, for example, Carcinogenesis vol. 13, No. 5, 751–758 (1992); or a N-acetylated or deacetylated 4-aminobiphenyl adduct capable of inhibiting DNA synthesis (see also, Id. 751–758); trivalent chromium, a trivalent chromium salt, a polycyclic aromatic hydrocarbon ("PAH") DNA adduct capable of inhibiting DNA replication, such as 7-bromomethyl-benz[a]anthracene ("BMA"), tris(2,3-dibromopropyl)phosphate ("Tris-BP"), 1,2-dibromo-3-chloropropane ("DBCP"), 2-bromoacrolein (2BA), benzo[a]pyrene-7,8-dihydrodiol-9-10-epoxide ("BPDE"), a platinum(II) halogen salt, N-hydroxy-2-amino-3-methylimidazo[4,5-f]-quinoline ("N-hydroxy-IQ"), and N-hydroxy-2-amino-1-methyl-6-phenylimidazo[4,5f]-pyridine ("N-hydroxy-PhIP"). Especially preferred "means for slowing or halting PCR amplification consist of UV light (+)-CC-1065 and (+)-CC-1065-(N3-Adenine). Particularly encompassed means are DNA adducts or polynucleotides comprising the DNA adducts from the polynucleotides or polynucleotides pool, which can be released or removed by a process including heating the solution comprising the polynucleotides prior to further processing.

In another aspect the present invention is directed to a method of producing recombinant proteins having biological activity by treating a sample comprising double-stranded template polynucleotides encoding a wild-type protein under conditions according to the present invention which provide for the production of hybrid or reassorted polynucleotides.

The invention also provides the use of polynucleotide shuffling to shuffle a population of viral genes (e.g., capsid proteins, spike glycoproteins, polymerases, and proteases) or viral genomes (e.g., paramyxoviridae, orthomyxoviridae, herpesviruses, retroviruses, reoviruses and rhinoviruses). In an embodiment, the invention provides a method for shuffling sequences encoding all or portions of immunogenic viral proteins to generate novel combinations of epitopes as well as novel epitopes created by recombination; such shuffled viral proteins may comprise epitopes or combinations of epitopes as well as novel epitopes created by recombination; such shuffled viral proteins may comprise epitopes or combinations of epitopes which are likely to arise in the natural environment as a consequence of viral evolution; (e.g., such as recombination of influenza virus strains).

The invention also provides a method suitable for shuffling polynucleotide sequences for generating gene therapy vectors and replication-defective gene therapy constructs, such as may be used for human gene therapy, including but not limited to vaccination vectors for DNA-based vaccination, as well as anti-neoplastic gene therapy and other general therapy formats.

The term "DNA shuffling" is used herein to indicate recombination between substantially homologous but non-identical sequences, in some embodiments DNA shuffling may involve crossover via non-homologous recombination, such as via cer/lox and/or flp/frt systems and the like.

The term "amplification" means that the number of copies of a polynucleotide is increased.

The term "identical" or "identity" means that two nucleic acid sequences have the same sequence or a complementary sequence. Thus, "areas of identity" means that regions or areas of a polynucleotide or the overall polynucleotide are identical or complementary to areas of another polynucleotide or the polynucleotide.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference "TATAC" and is complementary to a reference sequence "GTATA."

Genetic instability, as used herein, refers to the natural tendency of highly repetitive sequences to be lost through a process of reductive events generally involving sequence simplification through the loss of repeated sequences. Deletions tend to involve the loss of one copy of a repeat and everything between the repeats.

Quasi-repeated units, as used herein, refers to the repeats to be re-assorted and are by definition not identical. Indeed the method is proposed not only for practically identical encoding units produced by mutagenesis of the identical starting sequence, but also the reassortment of similar or related sequences which may diverge significantly in some regions. Nevertheless, if the sequences contain sufficient homologies to be reassorted by this approach, they can be referred to as "quasi-repeated" units.

Reductive reassortment, as used herein, refers to the increase in molecular diversity that is accrued through deletion (and/or insertion) events that are mediated by repeated sequences.

Repetitive Index (RI), as used herein, is the average number of copies of the quasi-repeated units contained in the cloning vector.

The term "related polynucleotides" means that regions or areas of the polynucleotides are identical and regions or areas of the polynucleotides are heterologous.

The term "population" as used herein means a collection of components such as polynucleotides, portions or polynucleotides or proteins. A "mixed population: means a collection of components which belong to the same family of nucleic acids or proteins (i.e., are related) but which differ in their sequence (i.e., are not identical) and hence in their biological activity.

The term "specific polynucleotide" means a polynucleotide having certain end points and having a certain nucleic acid sequence. Two polynucleotides wherein one polynucleotide has the identical sequence as a portion of the second polynucleotide but different ends comprises two different specific polynucleotides.

The following terms are used to describe the sequence relationships between two or more polynucleotides: "reference sequence," "comparison window," "sequence identity," "percentage of sequence identity," and "substantial identity." A "reference sequence" is a defined sequence used as a basis for a sequence comparison; a reference sequence may be a subset of a larger sequence, for example, as a segment of a full-length cDNA or gene sequence given in a sequence listing, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity.

A "comparison window," as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) *Adv. Appl. Math.* 2: 482 by the homology alignment algorithm of Needlemen and Wuncsch *J. Mol. Biol.* 48: 443 (1970), by the search of similarity method of Pearson and Lipman *Proc. Natl. Acad. Sci.* (*U.S.A.*) 85: 2444 (1988), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. This "substantial identity", as used herein, denotes a characteristic of a polynucleotide sequence, wherein the polynucleotide comprises a sequence having at least 80 percent sequence identity, preferably at least 85 percent identity, often 90 to 95 percent sequence identity, and most commonly at least 99 percent sequence identity as compared to a reference sequence of a comparison window of at least 25–50 nucleotides, wherein the percentage of sequence identity is calculated by comparing the reference sequence to the polynucleotide sequence which may include deletions or additions which total 20 percent or less of the reference sequence over the window of comparison.

"Conservative amino acid substitutions" refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "homologous" or "homeologous" means that one single-stranded nucleic acid nucleic acid sequence may hybridize to a complementary single-stranded nucleic acid sequence. The degree of hybridization may depend on a number of factors including the amount of identity between the sequences and the hybridization conditions such as temperature and salt concentrations as discussed later. Preferably the region of identity is greater than about 5 bp, more preferably the region of identity is greater than 10 bp.

The term "heterologous" means that one single-stranded nucleic acid sequence is unable to hybridize to another single-stranded nucleic acid sequence or its complement. Thus areas of heterology means that areas of polynucleotides or polynucleotides have areas or regions within their sequence which are unable to hybridize to another nucleic acid or polynucleotide. Such regions or areas are, for example areas of mutations.

The term "cognate" as used herein refers to a gene sequence that is evolutionarily and functionally related between species. For example but not limitation, in the human genome the human CD4 gene is the cognate gene to the mouse 3d4 gene, since the sequences and structures of these two genes indicate that they are highly homologous and both genes encode a protein which functions in signaling T cell activation through MHC class II-restricted antigen recognition.

The term "wild-type" means that the polynucleotide does not comprise any mutations. A "wild type" protein means that the protein will be active at a level of activity found in nature and will comprise the amino acid sequence found in nature.

The term "mutations" means changes in the sequence of a wild-type nucleic acid sequence or changes in the sequence of a peptide. Such mutations may be point mutations such as transitions or transversions. The mutations may be deletions, insertions or duplications.

In the polypeptide notation used herein, the left-hand direction is the amino terminal direction and the right-hand direction is the carboxy-terminal direction, in accordance with standard usage and convention. Similarly, unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the coding RNA transcript are referred to as "downstream sequences".

The term "naturally-occurring" as used herein as applied to the object refers to the fact that an object can be found in nature. For example, a polypeptide or polynucleotide sequence that is present in an organism (including viruses) that can be isolated from a source in nature and which has not been intentionally modified by man in the laboratory is naturally occurring. Generally, the term naturally occurring refers to an object as present in a non-pathological (undiseased) individual, such as would be typical for the species.

The term "agent" is used herein to denote a chemical compound, a mixture of chemical compounds, an array of spatially localized compounds (e.g., a VLSIPS peptide array, polynucleotide array, and/or combinatorial small molecule array), biological macromolecule, a bacteriophage peptide display library, a bacteriophage antibody (e.g., scFv) display library, a polysome peptide display library, or an extract made form biological materials such as bacteria, plants, fungi, or animal (particular mammalian) cells or tissues. Agents are evaluated for potential activity as antineoplastics, antiinflammatories or apoptosis modulators by inclusion in screening assays described hereinbelow. Agents are evaluated for potential activity as specific protein interaction inhibitors (i.e., an agent which selectively inhibits a binding interaction between two predetermined polypeptides but which doe snot substantially interfere with cell viability) by inclusion in screening assays described hereinbelow.

As used herein, "substantially pure" means an object species is the predominant species present (i.e., on a molar basis it is more abundant than any other individual macromolecular species in the composition), and preferably substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species. Solvent species, small molecules (<500 Daltons), and elemental ion species are not considered macromolecular species.

As used herein the term "physiological conditions" refers to temperature, pH, ionic strength, viscosity, and like biochemical parameters which are compatible with a viable organism, and/or which typically exist intracellularly in a viable cultured yeast cell or mammalian cell. For example, the intracellular conditions in a yeast cell grown under typical laboratory culture conditions are physiological conditions. Suitable in vitro reaction conditions for in vitro transcription cocktails are generally physiological conditions. In general, in vitro physiological conditions comprise 50–200 mM NaCl or KCl, pH 6.5–8.5, 20–45° C. and 0.001–10 mM divalent cation (e.g., $Mg^{++}$, $Ca^{++}$); preferably about 150 mM NaCl or KCl, pH 7.2–7.6, 5 mM divalent cation, and often include 0.01–1.0 percent nonspecific protein (e.g., BSA). A non-ionic detergent (Tween, NP-40, Triton X-100) can often be present, usually at about 0.001 to 2%, typically 0.05–0.2% (v/v). Particular aqueous conditions may be selected by the practitioner according to conventional methods. For general guidance, the following buffered aqueous conditions may be applicable: 10–250 mM NaCl, 5–50 mM Tris HCl, pH 5–8, with optional addition of divalent cation(s) and/or metal chelators and/or non-ionic detergents and/or membrane fractions and/or anti-foam agents and/or scintillants.

"Specific hybridization" is defined herein as the formation of hybrids between a first polynucleotide and a second polynucleotide (e.g., a polynucleotide having a distinct but substantially identical sequence to the first polynucleotide), wherein substantially unrelated polynucleotide sequences do not form hybrids in the mixture.

As used herein, the term "single-chain antibody" refers to a polypeptide comprising a $V_H$ domain and a $V_L$ domain in polypeptide linkage, generally liked via a spacer peptide (e.g., [Gly-Gly-Gly-Gly-Ser]$_x$), and which may comprise additional amino acid sequences at the amino- and/or carboxy-termini. For example, a single-chain antibody may comprise a tether segment for linking to the encoding polynucleotide. As an example, a scFv is a single-chain antibody. Single-chain antibodies are generally proteins consisting of one or more polypeptide segments of at least 10 contiguous amino substantially encoded by genes of the immunoglobulin superfamily (e.g., see *The Immunoglobulin Gene Superfamily*, A. F. Williams and A. N. Barclay, in *Immunoglobulin Genes*, T. Honjo, F. W. Alt, and THE. Rabbits, eds., (1989) Academic press: San Diego, Calif., pp. 361–368, which is incorporated herein by reference), most frequently encoded by a rodent, non-human primate, avian, porcine bovine, ovine, goat, or human heavy chain or light chain gene sequence. A functional single-chain antibody generally contains a sufficient portion of an immunoglobulin superfamily gene product so as to retain the property of binding to a specific target molecule, typically a receptor or antigen (epitope).

As used herein, the term "complementarity-determining region" and "CDR" refer to the art-recognized term as exemplified by the Kabat and Chothia CDR definitions also generally known as supervariable regions or hypervariable loops (Chothia and Leks (1987) *J. Mol. Biol.* 196; 901; Clothia et al. (1989) *Nature* 342; 877; E. A. Kabat et al., Sequences of Proteins of Immunological Interest (national Institutes of Health, Bethesda, Md.) (1987); and Tramontano et al. (1990) *J. Mol. Biolog.* 215; 175). Variable region domains typically comprise the amino-terminal approximately 105–115 amino acids of a naturally-occurring immunoglobulin chain (e.g., amino acids 1–110), although variable domains somewhat shorter or longer are also suitable for forming single-chain antibodies.

An immunoglobulin light or heavy chain variable region consists of a "framework" region interrupted by three hypervariable regions, also called CDR's. The extent of the framework region and CDR's have been precisely defined (see, "Sequences of Proteins of Immunological Interest," E. Kabat et al., 4th Ed., U.S. Department of Health and human services, Bethesda, Md. (1987)). The sequences of the framework regions of different light or heavy chains are relatively conserved within a specie. As used herein, a "human framework region" is a framework region that is substantially identical (about 85 or more, usually 90–95 or more) to the framework region of a naturally occurring human immunoglobulin. the framework region of an antibody, that is the combined framework regions of the constituent light and heavy chains, serves to position and align the CDR's. The CDR's are primarily responsible for binding to an epitope of an antigen.

As used herein, the term "variable segment" refers to a portion of a nascent peptide which comprises a random, pseudorandom, or defined kernal sequence. A variable segment"refers to a portion of a nascent peptide which comprises a random pseudorandom, or defined kernal sequence. A variable segment can comprise both variant and invariant residue positions, and the degree of residue variation at a variant residue position may be limited: both options are selected at the discretion of the practitioner. Typically, variable segments are about 5 to 20 amino acid residues in length (e.g., 8 to 10), although variable segments may be longer and may comprise antibody portions or receptor proteins, such as an antibody fragment, a nucleic acid binding protein, a receptor protein, and the like.

As used herein, "random peptide sequence" refers to an amino acid sequence composed of two or more amino acid monomers and constructed by a stochastic or random process. A random peptide can include framework or scaffolding motifs, which may comprise invariant sequences.

As used herein "random peptide library" refers to a set of polynucleotide sequences that encodes a set of random peptides, and to the set of random peptides encoded by those polynucleotide sequences, as well as the fusion proteins contain those random peptides.

As used herein, the term "pseudorandom" refers to a set of sequences that have limited variability, such that, for example, the degree of residue variability at another position, but any pseudorandom position is allowed some degree of residue variation, however circumscribed.

As used herein, the term "defined sequence framework" refers to a set of defined sequences that are selected on a non-random basis, generally on the basis of experimental data or structural data; for example, a defined sequence framework may comprise a set of amino acid sequences that are predicted to form a β-sheet structure or may comprise a leucine zipper heptad repeat motif, a zinc-finger domain, among other variations. A "defined sequence kernal" is a set of sequences which encompass a limited scope of variability. Whereas (1) a completely random 10-mer sequence of the 20 conventional amino acids can be any of $(20)^{10}$ sequences, and (2) a pseudorandom 10-mer sequence of the 20 conventional amino acids can be any of $(20)^{10}$ sequences but will exhibit a bias for certain residues at certain positions and/or overall, (3) a defined sequence kernal is a subset of sequences if each residue position was allowed to be any of the allowable 20 conventional amino acids (and/or allowable unconventional amino/imino acids). A defined sequence kernal generally comprises variant and invariant residue positions and/or comprises variant residue positions which can comprise a residue selected from a defined subset of amino acid residues), and the like, either segmentally or over the entire length of the individual selected library member sequence. Defined sequence kernels can refer to either amino acid sequences or polynucleotide sequences. Of illustration and not limitation, the sequences $(NNK)_{10}$ and $(NNM)_{10}$, wherein N represents A, T, G, or C; K represents G or T; and M represents A or C, are defined sequence kernels.

As used herein "epitope" refers to that portion of an antigen or other macromolecule capable of forming a binding interaction that interacts with the variable region binding body of an antibody. Typically, such binding interaction is manifested as an intermolecular contact with one or more amino acid residues of a CDR.

As used herein, "receptor" refers to a molecule that has an affinity for a given ligand. Receptors can be naturally occurring or synthetic molecules. Receptors can be employed in an unaltered state or as aggregates with other species. Receptors can be attached, covalently or non-covalently, to a binding member, either directly or via a specific binding substance. Examples of receptors include, but are not limited to, antibodies, including monoclonal antibodies and antisera reactive with specific antigenic determinants (such as on viruses, cells, or other materials), cell membrane receptors, complex carbohydrates and glycoproteins, enzymes, and hormone receptors.

As used herein "ligand" refers to a molecule, such as a random peptide or variable segment sequence, that is recognized by a particular receptor. As one of skill in the art will recognize, a molecule (or macromolecular complex) can be both a receptor and a ligand. In general, the binding partner having a smaller molecular weight is referred to as the ligand and the binding partner having a greater molecular weight is referred to as a receptor.

As used herein, "linker" or "spacer" refers to a molecule or group of molecules that connects two molecules, such as a DNA binding protein and a random peptide, and serves to place the two molecules in a preferred configuration, e.g., so that the random peptide can bind to a receptor with minimal steric hindrance from the DNA binding protein.

Methodology

Nucleic acid shuffling is a method for in vitro or in vivo homologous recombination of pools of shorter or smaller polynucleotides to produce a polynucleotide or polynucleotides. Mixtures of related nucleic acid sequences or polynucleotides are subjected to sexual PCR to provide random polynucleotides, and reassembled to yield a library or mixed population of recombinant hybrid nucleic acid molecules or polynucleotides.

In contrast to cassette mutagenesis, only shuffling and error-prone PCR allow one to mutate a pool of sequences blindly (without sequence information other than primers).

The advantage of the mutagenic shuffling of this invention over error-prone PCR alone for repeated selection can best be explained with an example from antibody engineering. In FIG. 1 is shown a prior art schematic diagram of DNA shuffling as compared with error-prone PCR (not sexual PCR). The initial library of selected pooled sequences can consist of related sequences of diverse origin (i.e. antibodies from naive mRNA) or can be derived by any type of mutagenesis (including shuffling) of a single antibody gene. A collection of selected complementarity determining regions ("CDRs") is obtained after the first round of affinity selection (FIG. 1). In the diagram the thick CDRs confer onto the antibody molecule increased affinity for the antigen. Shuffling allows the free combinatorial association of all of the CDR1s with all of the CDR2s with all of the CDR3s, for example.

This method differs from error-prone PCR, in that it is an inverse chain reaction. In error-prone PCR, the number of polymerase start sites and the number of molecules grows exponentially. However, the sequence of the polymerase start sites and the sequence of the molecules remains essentially the same. In contrast, in nucleic acid reassembly or shuffling of random polynucleotides the number of start sites and the number (but not size) of the random polynucleotides decreases over time. For polynucleotides derived from whole plasmids the theoretical endpoint is a single, large concatemeric molecule.

Since cross-overs occur at regions of homology, recombination will primarily occur between members of the same sequence family. This discourages combinations of CDRs that are grossly incompatible (e.g., directed against different epitopes of the same antigen). It is contemplated that multiple families of sequences can be shuffled in the same reaction. Further, shuffling generally conserves the relative order, such that, for example, CDR1 will not be found in the position of CDR2.

Rare shufflants will contain a large number of the best (eg. highest affinity) CDRs and these rare shufflants may be selected based on their superior affinity (FIG. 1).

CDRs from a pool of 100 different selected antibody sequences can be permutated in up to 1006 different ways. This large number of permutations cannot be represented in a single library of DNA sequences. Accordingly, it is contemplated that multiple cycles of DNA shuffling and selection may be required depending on the length of the sequence and the sequence diversity desired.

Error-prone PCR, in contrast, keeps all the selected CDRs in the same relative sequence (FIG. 1), generating a much smaller mutant cloud.

The template polynucleotide which may be used in the methods of this invention may be DNA or RNA. It may be of various lengths depending on the size of the gene or shorter or smaller polynucleotide to be recombined or reassembled. Preferably, the template polynucleotide is from 50 bp to 50 kb. It is contemplated that entire vectors containing the nucleic acid encoding the protein of interest can be used in the methods of this invention, and in fact have been successfully used.

The template polynucleotide may be obtained by amplification using the PCR reaction (U.S. Pat. Nos. 4,683,202 and 4,683,195) or other amplification or cloning methods. However, the removal of free primers from the PCR products before subjecting them to pooling of the PCR products and sexual PCR may provide more efficient results. Failure to adequately remove the primers from the original pool before sexual PCR can lead to a low frequency of crossover clones.

The template polynucleotide often should be double-stranded. A double-stranded nucleic acid molecule is recommended to ensure that regions of the resulting single-stranded polynucleotides are complementary to each other and thus can hybridize to form a double-stranded molecule.

It is contemplated that single-stranded or double-stranded nucleic acid polynucleotides having regions of identity to the template polynucleotide and regions of heterology to the template polynucleotide may be added to the template polynucleotide, at this step. It is also contemplated that two different but related polynucleotide templates can be mixed at this step.

The double-stranded polynucleotide template and any added double-or single-stranded polynucleotides are subjected to sexual PCR which includes slowing or halting to provide a mixture of from about 5 bp to 5 kb or more. Preferably the size of the random polynucleotides is from about 10 bp to 1000 bp, more preferably the size of the polynucleotides is from about 20 bp to 500 bp.

Alternatively, it is also contemplated that double-stranded nucleic acid having multiple nicks may be used in the methods of this invention. A nick is a break in one strand of the double-stranded nucleic acid. The distance between such nicks is preferably 5 bp to 5 kb, more preferably between 10 bp to 1000 bp. This can provide areas of self-priming to produce shorter or smaller polynucleotides to be included with the polynucleotides resulting from random primers, for example.

The concentration of any one specific polynucleotide will not be greater than 1% by weight of the total polynucleotides, more preferably the concentration of any one specific nucleic acid sequence will not be greater than 0.1% by weight of the total nucleic acid.

The number of different specific polynucletides in the mixture will be at least about 100, preferably at least about 500, and more preferably at least about 1000.

At this step single-stranded or double-stranded polynucleotides, either synthetic or natural, may be added to the random double-stranded shorter or smaller polynucleotides in order to increase the heterogeneity of the mixture of polynucleotides.

It is also contemplated that populations of double-stranded randomly broken polynucleotides may be mixed or combined at this step with the polynucleotides from the sexual PCR process and optionally subjected to one or more additional sexual PCR cycles.

Where insertion of mutations into the template polynucleotide is desired, single-stranded or double-stranded polynucleotides having a region of identity to the template polynucleotide and a region of heterology to the template polynucleotide may be added in a 20 fold excess by weight as compared to the total nucleic acid, more preferably the single-stranded polynucleotides may be added in a 10 fold excess by weight as compared to the total nucleic acid.

Where a mixture of different but related template polynucleotides is desired, populations of polynucleotides from each of the templates may be combined at a ratio of less than about 1:100, more preferably the ratio is less than about 1:40. For example, a backcross of the wild-type polynucleotide with a population of mutated polynucleotide may be desired to eliminate neutral mutations (e.g., mutations yielding an insubstantial alteration in the phenotypic property being selected for). In such an example, the ratio of randomly provided wild-type polynucleotides which may be added to the randomly provided sexual PCR cycle hybrid polynucleotides is approximately 1:1 to about 100:1, and more preferably from 1:1 to 40:1.

The mixed population of random polynucleotides are denatured to form single-stranded polynucleotides and then re-annealed. Only those single-stranded polynucleotides having regions of homology with other single-stranded polynucleotides will re-anneal.

The random polynucleotides may be denatured by heating. One skilled in the art could determine the conditions necessary to completely denature the double-stranded nucleic acid. Preferably the temperature is from 80° C. to 100° C., more preferably the temperature is from 90° C. to 96° C. other methods which may be used to denature the polynucleotides include pressure (36) and pH.

The polynucleotides may be re-annealed by cooling. Preferably the temperature is from 20° C. to 75° C., more preferably the temperature is from 40° C. to 65° C. If a high frequency of crossovers is needed based on an average of only 4 consecutive bases of homology, recombination can be forced by using a low annealing temperature, although the process becomes more difficult. The degree of renaturation which occurs will depend on the degree of homology between the population of single-stranded polynucleotides.

Renaturation can be accelerated by the addition of polyethylene glycol ("PEG") or salt. The salt concentration is preferably from 0 mM to 200 mM, more preferably the salt concentration is from 10 mM to 100 mm. The salt may be KCl or NaCl. The concentration of PEG is preferably from 0% to 20%, more preferably from 5% to 10%.

The annealed polynucleotides are next incubated in the presence of a nucleic acid polymerase and dNTP's (i.e. dATP, dCTP, DGTP and dTTP). The nucleic acid polymerase may be the Klenow fragment, the Taq polymerase or any other DNA polymerase known in the art.

The approach to be used for the assembly depends on the minimum degree of homology that should still yield cross-overs. If the areas of identity are large, Taq polymerase can be used with an annealing temperature of between 45–65° C. If the areas of identity are small, Klenow polymerase can be used with an annealing temperature of between 20–30° C. One skilled in the art could vary the temperature of annealing to increase the number of cross-overs achieved.

The polymerase may be added to the random polynucleotides prior to annealing, simultaneously with annealing or after annealing.

The cycle of denaturation, renaturation and incubation in the presence of polymerase is referred to herein as shuffling or reassembly of the nucleic acid. This cycle is repeated for a desired number of times. Preferably the cycle is repeated from 2 to 50 times, more preferably the sequence is repeated from 10 to 40 times.

The resulting nucleic acid is a larger double-stranded polynucleotide of from about 50 bp to about 100 kb, preferably the larger polynucleotide is from 500 bp to 50 kb.

This larger polynucleotides may contain a number of copies of a polynucleotide having the same size as the template polynucleotide in tandem. This concatemeric polynucleotide is then denatured into single copies of the template polynucleotide. The result will be a population of polynucleotides of approximately the same size as the template polynucleotide. The population will be a mixed population where single or double-stranded polynucleotides having an area of identity and an area of heterology have been added to the template polynucleotide prior to shuffling.

These polynucleotides are then cloned into the appropriate vector and the ligation mixture used to transform bacteria.

It is contemplated that the single polynucleotides may be obtained from the larger concatemeric polynucleotide by amplification of the single polynucleotide prior to cloning by a variety of methods including PCR (U.S. Pat. Nos. 4,683,195 and 4,683,202), rather than by digestion of the concatemer.

The vector used for cloning is not critical provided that it will accept a polynucleotide of the desired size. If expression of the particular polynucleotide is desired, the cloning vehicle should further comprise transcription and translation signals next to the site of insertion of the polynucleotide to allow expression of the polynucleotide in the host cell. Preferred vectors include the pUC series and the pBR series of plasmids.

The resulting bacterial population will include a number of recombinant polynucleotides having random mutations. This mixed population may be tested to identify the desired recombinant polynucleotides. The method of selection will depend on the polynucleotide desired.

For example, if a polynucleotide which encodes a protein with increased binding efficiency to a ligand is desired, the proteins expressed by each of the portions of the polynucleotides in the population or library may be tested for their ability to bind to the ligand by methods known in the art (i.e. panning, affinity chromatography). If a polynucleotide which encodes for a protein with increased drug resistance is desired, the proteins expressed by each of the polynucleotides in the population or library may be tested for their ability to confer drug resistance to the host organism. One skilled in the art, given knowledge of the desired protein, could readily test the population to identify polynucleotides which confer the desired properties onto the protein.

It is contemplated that one skilled in the art could use a phage display system in which fragments of the protein are expressed as fusion proteins on the phage surface (Pharmacia, Milwaukee Wis.). The recombinant DNA molecules are cloned into the phage DNA at a site which results in the transcription of a fusion protein a portion of which is encoded by the recombinant DNA molecule. The phage containing the recombinant nucleic acid molecule undergoes replication and transcription in the cell. The leader sequence of the fusion protein directs the transport of the fusion protein to the tip of the phage particle. Thus the fusion protein which is partially encoded by the recombinant DNA molecule is displayed on the phage particle for detection and selection by the methods described above.

It is further contemplated that a number of cycles of nucleic acid shuffling may be conducted with polynucleotides from a sub-population of the first population, which sub-population contains DNA encoding the desired recombinant protein. In this manner, proteins with even higher binding affinities or enzymatic activity could be achieved.

It is also contemplated that a number of cycles of nucleic acid shuffling may be conducted with a mixture of wild-type polynucleotides and a sub-population of nucleic acid from the first or subsequent rounds of nucleic acid shuffling in order to remove any silent mutations from the sub-population.

Any source of nucleic acid, in purified form can be utilized as the starting nucleic acid. Thus the process may employ DNA or RNA including messenger RNA, which DNA or RNA may be single or double stranded. In addition, a DNA-RNA hybrid which contains one strand of each may be utilized. The nucleic acid sequence may be of various lengths depending on the size of the nucleic acid sequence to be mutated. Preferably the specific nucleic acid sequence is from 50 to 50000 base pairs. It is contemplated that entire vectors containing the nucleic acid encoding the protein of interest may be used in the methods of this invention.

The nucleic acid may be obtained from any source, for example, from plasmids such a pBR322, from cloned DNA or RNA or from natural DNA or RNA from any source including bacteria, yeast, viruses and higher organisms such as plants or animals. DNA or RNA may be extracted from blood or tissue material. The template polynucleotide may be obtained by amplification using the polynucleotide chain reaction (PCR) (U.S. Pat. Nos. 4,683,202 and 4,683,195). Alternatively, the polynucleotide may be present in a vector present in a cell and sufficient nucleic acid may be obtained by culturing the cell and extracting the nucleic acid from the cell by methods known in the art.

Any specific nucleic acid sequence can be used to produce the population of hybrids by the present process. It is only necessary that a small population of hybrid sequences of the specific nucleic acid sequence exist or be created prior to the present process.

The initial small population of the specific nucleic acid sequences having mutations may be created by a number of different methods. Mutations may be created by error-prone PCR. Error-prone PCR uses low-fidelity polymerization conditions to introduce a low level of point mutations randomly over a long sequence. Alternatively, mutations can be introduced into the template polynucleotide by oligonucleotide-directed mutagenesis. In oligonucleotide-directed mutagenesis, a short sequence of the polynucleotide is removed from the polynucleotide using restriction enzyme digestion and is replaced with a synthetic polynucleotide in which various bases have been altered from the original sequence. The polynucleotide sequence can also be altered by chemical mutagenesis. Chemical mutagens include, for example, sodium bisulfite, nitrous acid, hydroxylamine, hydrazine or formic acid. other agents which are analogues of nucleotide precursors include nitrosoguanidine, 5-bromouracil, 2-aminopurine, or acridine. Generally, these agents are added to the PCR reaction in place of the nucleotide precursor thereby mutating the sequence. Intercalating agents such as proflavine, acriflavine, quinacrine and the like can also be used. Random mutagenesis of the polynucleotide sequence can also be achieved by irradiation with X-rays or ultraviolet light. Generally, plasmid polynucleotides so mutagenized are introduced into $E.$ $coli$ and propagated as a pool or library of hybrid plasmids.

Alternatively the small mixed population of specific nucleic acids may be found in nature in that they may consist of different alleles of the same gene or the same gene from different related species (i.e., cognate genes). Alternatively, they may be related DNA sequences found within one species, for example, the immunoglobulin genes.

Once the mixed population of the specific nucleic acid sequences is generated, the polynucleotides can be used directly or inserted into an appropriate cloning vector, using techniques well-known in,the art.

The choice of vector depends on the size of the polynucleotide sequence and the host cell to be employed in the methods of this invention. The templates of this invention may be plasmids, phages, cosmids, phagemids, viruses (e.g., retroviruses, parainfluenzavirus, herpesviruses, reoviruses, paramyxoviruses, and the like), or selected portions thereof (e.g., coat protein, spike glycoprotein, capsid protein). For example, cosmids and phagemids are preferred where the specific nucleic acid sequence to be mutated is larger because these vectors are able to stably propagate large polynucleotides.

If the mixed population of the specific nucleic acid sequence is cloned into a vector it can be clonally amplified by inserting each vector into a host cell and allowing the host cell to amplify the vector. This is referred to as clonal amplification because while the absolute number of nucleic acid sequences increases, the number of hybrids does not increase. Utility can be readily determined by screening expressed polypeptides.

The DNA shuffling method of this invention can be performed blindly on a pool of unknown sequences. By adding to the reassembly mixture oligonucleotides (with ends that are homologous to the sequences being reassembled) any sequence mixture can be incorporated at any specific position into another sequence mixture. Thus, it is contemplated that mixtures of synthetic oligonucleotides, PCR polynucleotides or even whole genes can be mixed into another sequence library at defined positions. The insertion of one sequence (mixture) is independent from the insertion of a sequence in another part of the template. Thus, the degree of recombination, the homology required, and the diversity of the library can be independently and simultaneously varied along the length of the reassembled DNA.

This approach of mixing two genes may be useful for the humanization of antibodies from murine hybridomas. The approach of mixing two genes or inserting alternative sequences into genes may be useful for any therapeutically used protein, for example, interleukin I, antibodies, tPA and growth hormone. The approach may also be useful in any nucleic acid for example, promoters or introns or 31 untranslated region or 51 untranslated regions of genes to increase expression or alter specificity of expression of proteins. The approach may also be used to mutate ribozymes or aptamers.

Shuffling requires the presence of homologous regions separating regions of diversity. Scaffold-like protein structures may be particularly suitable for shuffling. The conserved scaffold determines the overall folding by self-association, while displaying relatively unrestricted loops that mediate the specific binding. Examples of such scaffolds are the immunoglobulin beta-barrel, and the four-helix bundle which are well-known in the art. This shuffling can be used to create scaffold-like proteins with various combinations of mutated sequences for binding.

In vitro Shuffling

The equivalents of some standard genetic matings may also be performed by shuffling in vitro. For example, a "molecular backcross" can be performed by repeatedly mixing the hybrid's nucleic acid with the wild-type nucleic acid while selecting for the mutations of interest. As in traditional breeding, this approach can be used to combine phenotypes from different sources into a background of choice. It is useful, for example, for the removal of neutral mutations that affect unselected characteristics (i.e. immunogenicity). Thus it can be useful to determine which mutations in a protein are involved in the enhanced biological activity and which are not, an advantage which cannot be achieved by error-prone mutagenesis or cassette mutagenesis methods.

Large, functional genes can be assembled correctly from a mixture of small random polynucleotides. This reaction may be of use for the reassembly of genes from the highly fragmented DNA of fossils. In addition random nucleic acid fragments from fossils may be combined with polynucleotides from similar genes from related species.

It is also contemplated that the method of this invention can be used for the in vitro amplification of a whole genome from a single cell as is needed for a variety of research and diagnostic applications. DNA amplification by PCR is in practice limited to a length of about 40 kb. Amplification of a whole genome such as that of $E.$ $coli$ (5,000 kb) by PCR would require about 250 primers yielding 125 forty kb polynucleotides. This approach is not practical due to the unavailability of sufficient sequence data. On the other hand, random production of polynucleotides of the genome with sexual PCR cycles, followed by gel purification of small polynucleotides will provide a multitude of possible primers. Use of this mix of random small polynucleotides as primers in a PCR reaction alone or with the whole genome as the template should result in an inverse chain reaction with the theoretical endpoint of a single concatemer containing many copies of the genome.

100 fold amplification in the copy number and an average polynucleotide size of greater than 50 kb may be obtained when only random polynucleotides are used. It is thought that the larger concatemer is generated by overlap of many smaller polynucleotides. The quality of specific PCR products obtained using synthetic primers will be indistinguishable from the product obtained from unamplified DNA. It is expected that this approach will be useful for the mapping of genomes.

The polynucleotide to be shuffled can be produced as random or non-random polynucleotides, at the discretion of the practitioner.

In vivo Shuffling

In an embodiment of in vivo shuffling, the mixed population of the specific nucleic acid sequence is introduced into bacterial or eukaryotic cells under conditions such that at least two different nucleic acid sequences are present in each host cell. The polynucleotides can be introduced into the host cells by a variety of different methods. The host cells can be transformed with the smaller polynucleotides using methods known in the art, for example treatment with calcium chloride. If the polynucleotides are inserted into a phage genome, the host cell can be transfected with the recombinant phage genome having the specific nucleic acid sequences. Alternatively, the nucleic acid sequences can be introduced into the host cell using electroporation, transfection, lipofection, biolistics, conjugation, and the like.

In general, in this embodiment, the specific nucleic acids sequences will be present in vectors which are capable of stably replicating the sequence in the host cell. In addition, it is contemplated that the vectors will encode a marker gene such that host cells having the vector can be selected. This ensures that the mutated specific nucleic acid sequence can be recovered after introduction into the host cell. However, it is contemplated that the entire mixed population of the specific nucleic acid sequences need not be present on a vector sequence. Rather only a sufficient number of sequences need be cloned into vectors to ensure that after introduction of the polynucleotides into the host cells each host cell contains one vector having at least one specific nucleic acid sequence present therein. It is also contemplated that rather than having a subset of the population of the specific nucleic acids sequences cloned into vectors, this subset may be already stably integrated into the host cell.

It has been found that when two polynucleotides which have regions of identity are inserted into the host cells homologous recombination occurs between the two polynucleotides. Such recombination between the two mutated specific nucleic acid sequences will result in the production of double or triple hybrids in some situations.

It has also been found that the frequency of recombination is increased if some of the mutated specific nucleic acid sequences are present on linear nucleic acid molecules. Therefore, in a preferred embodiment, some of the specific nucleic acid sequences are present on linear polynucleotides.

After transformation, the host cell transformants are placed under selection to identify those host cell transformants which contain mutated specific nucleic acid sequences having the qualities desired. For example, if increased resistance to a particular drug is desired then the transformed host cells may be subjected to increased concentrations of the particular drug and those transformants producing mutated proteins able to confer increased drug resistance will be selected. If the enhanced ability of a particular protein to bind to a receptor is desired, then expression of the protein can be induced from the transformants and the resulting protein assayed in a ligand binding assay by methods known in the art to identify that subset of the mutated population which shows enhanced binding to the ligand. Alternatively, the protein can be expressed in another system to ensure proper processing.

Once a subset of the first recombined specific nucleic acid sequences (daughter sequences) having the desired characteristics are identified, they are then subject to a second round of recombination.

In the second cycle of recombination, the recombined specific nucleic acid sequences may be mixed with the original mutated specific nucleic acid sequences (parent sequences) and the cycle repeated as described above. In this way a set of second recombined specific nucleic acids sequences can be identified which have enhanced characteristics or encode for proteins having enhanced properties. This cycle can be repeated a number of times as desired.

It is also contemplated that in the second or subsequent recombination cycle, a backcross can be performed. A molecular backcross can be performed by mixing the desired specific nucleic acid sequences with a large number of the wild-type sequence, such that at least one wild-type nucleic acid sequence and a mutated nucleic acid sequence are present in the same host cell after transformation. Recombination with the wild-type specific nucleic acid sequence will eliminate those neutral mutations that may affect unselected characteristics such as immunogenicity but not the selected characteristics.

In another embodiment of this invention, it is contemplated that during the first round a subset of the specific nucleic acid sequences can be generated as smaller polynucleotides by slowing or halting their PCR amplification prior to introduction into the host cell. The size of the polynucleotides must be large enough to contain some regions of identity with the other sequences so as to homologously recombine with the other sequences. The size of the polynucleotides will range from 0.03 kb to 100 kb more preferably from 0.2 kb to 10 kb. It is also contemplated that in subsequent rounds, all of the specific nucleic acid sequences other than the sequences selected from the previous round may be utilized to generate PCR polynucleotides prior to introduction into the host cells.

The shorter polynucleotide sequences can be single-stranded or double-stranded. If the sequences were originally single-stranded and have become double-stranded they can be denatured with heat, chemicals or enzymes prior to insertion into the host cell. The reaction conditions suitable for separating the strands of nucleic acid are well known in the art.

The steps of this process can be repeated indefinitely, being limited only by the number of possible hybrids which can be achieved. After a certain number of cycles, all possible hybrids will have been achieved and further cycles are redundant.

In an embodiment the same mutated template nucleic acid is repeatedly recombined and the resulting recombinants selected for the desired characteristic.

Therefore, the initial pool or population of mutated template nucleic acid is cloned into a vector capable of replicating in a bacteria such as *E. coli*. The particular vector is not essential, so long as it is capable of autonomous replication in *E. coli*. In a preferred embodiment, the vector is designed to allow the expression and production of any protein encoded by the mutated specific nucleic acid linked to the vector. It is also preferred that the vector contain a gene encoding for a selectable marker.

The population of vectors containing the pool of mutated nucleic acid sequences is introduced into the *E. coli* host cells. The vector nucleic acid sequences may be introduced by transformation, transfection or infection in the case of phage. The concentration of vectors used to transform the bacteria is such that a number of vectors is introduced into each cell. Once present in the cell, the efficiency of homologous recombination is such that homologous recombination occurs between the various vectors. This results in the generation of hybrids (daughters) having a combination of mutations which differ from the original parent mutated sequences.

The host cells are then clonally replicated and selected for the marker gene present on the vector. Only those cells having a plasmid will grow under the selection.

The host cells which contain a vector are then tested for the presence of favorable mutations. Such testing may consist of placing the cells under selective pressure, for example, if the gene to be selected is an improved drug resistance gene. If the vector allows expression of the protein encoded by the mutated nucleic acid sequence, then such selection may include allowing expression of the protein so encoded, isolation of the protein and testing of the protein to determine whether, for example, it binds with increased efficiency to the ligand of interest.

Once a particular daughter mutated nucleic acid sequence has been identified which confers the desired characteristics, the nucleic acid is isolated either already linked to the vector or separated from the vector. This nucleic acid is then mixed with the first or parent population of nucleic acids and the cycle is repeated.

It has been shown that by this method nucleic acid sequences having enhanced desired properties can be selected.

In an alternate embodiment, the first generation of hybrids are retained in the cells and the parental mutated sequences are added again to the cells. Accordingly, the first cycle of Embodiment I is conducted as described above. However, after the daughter nucleic acid sequences are identified, the host cells containing these sequences are retained.

The parent mutated specific nucleic acid population, either as polynucleotides or cloned into the same vector is introduced into the host cells already containing the daughter nucleic acids. Recombination is allowed to occur in the cells and the next generation of recombinants, or granddaughters are selected by the methods described above.

This cycle can be repeated a number of times until the nucleic acid or peptide having the desired characteristics is obtained. It is contemplated that in subsequent cycles, the population of mutated sequences which are added to the preferred hybrids may come from the parental hybrids or any subsequent generation.

In an alternative embodiment, the invention provides a method of conducting a "molecular" backcross of the obtained recombinant specific nucleic acid in order to eliminate any neutral mutations. Neutral mutations are those mutations which do not confer onto the nucleic acid or peptide the desired properties. Such mutations may however confer on the nucleic acid or peptide undesirable characteristics. Accordingly, it is desirable to eliminate such neutral mutations. The method of this invention provide a means of doing so.

In this embodiment, after the hybrid nucleic acid, having the desired characteristics, is obtained by the methods of the embodiments, the nucleic acid, the vector having the nucleic acid or the host cell containing the vector and nucleic acid is isolated.

The nucleic acid or vector is then introduced into the host cell with a large excess of the wild-type nucleic acid. The nucleic acid of the hybrid and the nucleic acid of the wild-type sequence are allowed to recombine. The resulting recombinants are placed under the same selection as the hybrid nucleic acid. Only those recombinants which retained the desired characteristics will be selected. Any silent mutations which do not provide the desired characteristics will be lost through recombination with the wild-type DNA. This cycle can be repeated a number of times until all of the silent mutations are eliminated.

Thus the methods of this invention can be used in a molecular backcross to eliminate unnecessary or silent mutations.

Utility

The in vivo recombination method of this invention can be performed blindly on a pool of unknown hybrids or alleles of a specific polynucleotide or sequence. However, it is not necessary to know the actual DNA or RNA sequence of the specific polynucleotide.

The approach of using recombination within a mixed population of genes can be useful for the generation of any useful proteins, for example, interleukin I, antibodies, tPA and growth hormone. This approach may be used to generate proteins having altered specificity or activity. The approach may also be useful for the generation of hybrid nucleic acid sequences, for example, promoter regions, introns, exons, enhancer sequences, 31 untranslated regions or 51 untranslated regions of genes. Thus this approach may be used to generate genes having increased rates of expression. This approach may also be useful in the study of repetitive DNA sequences. Finally, this approach may be useful to mutate ribozymes or aptamers.

Scaffold-like regions separating regions of diversity in proteins may be particularly suitable for the methods of this invention. The conserved scaffold determines the overall folding by self-association, while displaying relatively unrestricted loops that mediate the specific binding. Examples of such scaffolds are the immunoglobulin beta barrel, and the four-helix bundle. The methods of this invention can be used to create scaffold-like proteins with various combinations of mutated sequences for binding.

The equivalents of some standard genetic matings may also be performed by the methods of this invention. For example, a "molecular" backcross can be performed by repeated mixing of the hybrid's nucleic acid with the wild-type nucleic acid while selecting for the mutations of interest. As in traditional breeding, this approach can be used to combine phenotypes from different sources into a background of choice. It is useful, for example, for the removal of neutral mutations that affect unselected characteristics (i.e. immunogenicity). Thus it can be useful to determine which mutations in a protein are involved in the enhanced biological activity and which are not.

Peptide Display Methods

The present method can be used to shuffle, by in vitro and/or in vivo recombination by any of the disclosed methods, and in any combination, polynucleotide sequences selected by peptide display methods, wherein an associated polynucleotide encodes a displayed peptide which is screened for a phenotype (e.g., for affinity for a predetermined receptor (ligand).

An increasingly important aspect of bio-pharmaceutical drug development and molecular biology is the identification of peptide structures, including the primary amino acid sequences, of peptides or peptidomimetics that interact with biological macromolecules. one method of identifying peptides that possess a desired structure or functional property, such as binding to a predetermined biological macromolecule (e.g., a receptor), involves the screening of a large library or peptides for individual library members which possess the desired structure or functional property conferred by the amino acid sequence of the peptide.

In addition to direct chemical synthesis methods for generating peptide libraries, several recombinant DNA methods also have been reported. One type involves the display of a peptide sequence, antibody, or other protein on the surface of a bacteriophage particle or cell. Generally, in these methods each bacteriophage particle or cell serves as an individual library member displaying a single species of displayed peptide in addition to the natural bacteriophage or cell protein sequences. Each bacteriophage or cell contains the nucleotide sequence information encoding the particular displayed peptide sequence; thus, the displayed peptide sequence can be ascertained by nucleotide sequence determination of an isolated library member.

A well-known peptide display method involves the presentation of a peptide sequence on the surface of a filamentous bacteriophage, typically as a fusion with a bacteriophage coat protein. The bacteriophage library can be incubated with an immobilized, predetermined macromolecule or small molecule (e.g., a receptor) so that bacteriophage particles which present a peptide sequence that binds to the immobilized macromolecule can be differentially partitioned from those that do not present peptide sequences that bind to the predetermined macromolecule. The bacteriophage particles (i.e., library members) which are bound to the immobilized macromolecule are then recovered and replicated to amplify the selected bacteriophage sub-population for a subsequent round of affinity enrichment and phage replication. After several rounds of affinity enrichment and phage replication, the bacteriophage library members that are thus selected are isolated and the nucleotide sequence encoding the displayed peptide sequence is determined, thereby identifying the sequence(s) of peptides that bind to the predetermined macromolecule (e.g., receptor). Such methods are further described in PCT patent publication Nos. 91/17271, 91/18980, and 91/19818 and 93/08278.

The latter PCT publication describes a recombinant DNA method for the display of peptide ligands that involves the production of a library of fusion proteins with each fusion protein composed of a first polypeptide portion, typically comprising a variable sequence, that is available for potential binding to a predetermined macromolecule, and a second polypeptide portion that binds to DNA, such as the DNA vector encoding the individual fusion protein. When transformed host cells are cultured under conditions that allow for expression of the fusion protein, the fusion protein binds to the DNA vector encoding it. Upon lysis of the host cell, the fusion protein/vector DNA complexes can be screened against a predetermined macromolecule in much the same way as bacteriophage particles are screened in the phage-based display system, with the replication and sequencing of the DNA vectors in the selected fusion protein/vector DNA complexes serving as the basis for identification of the selected library peptide sequence(s).

Other systems for generating libraries of peptides and like polymers have aspects of both the recombinant and in vitro chemical synthesis methods. In these hybrid methods, cell-free enzymatic machinery is employed to accomplish the in vitro synthesis of the library members (i.e., peptides or polynucleotides). In one type of method, RNA molecules with the ability to bind a predetermined protein or a predetermined dye molecule were selected by alternate rounds of selection and PCR amplification (Tuerk and Gold (1990) *Science* 249: 505; Ellington and Szostak (1990) *Nature* 346: 818). A similar technique was used to identify DNA sequences which bind a predetermined human transcription factor (Thiesen and Bach (1990) *Nucleic Acids Res.* 18: 3203; Beaudry and Joyce (1992) *Science* 257: 635; PCT patent publication Nos. 92/05258 and 92/14843). In a similar fashion, the technique of in vitro translation has been used to synthesize proteins of interest and has been proposed as a method for generating large libraries of peptides. These methods which rely upon in vitro translation, generally comprising stabilized polysome complexes, are described further in PCT patent publication Nos. 88/08453, 90/05785, 90/07003, 91/02076, 91/05058, and 92/02536. Applicants have described methods in which library members comprise a fusion protein having a first polypeptide portion with DNA binding activity and a second polypeptide portion having the library member unique peptide sequence; such methods are suitable for use in cell-free in vitro selection formats, among others.

The displayed peptide sequences can be of varying lengths, typically from 3–5000 amino acids long or longer, frequently from 5–100 amino acids long, and often from about 8–15 amino acids long. A library can comprise library members having varying lengths of displayed peptide sequence, or may comprise library members having a fixed length of displayed peptide sequence. Portions or all of the displayed peptide sequence(s) can be random, pseudorandom, defined set kernal, fixed, or the like. The present display methods include methods for in vitro and in vivo display of single-chain antibodies, such as nascent scFv on polysomes or scfv displayed on phage, which enable large-scale screening of scfv libraries having broad diversity of variable region sequences and binding specificities.

The present invention also provides random, pseudorandom, and defined sequence framework peptide libraries and methods for generating and screening those libraries to identify useful compounds (e.g., peptides, including single-chain antibodies) that bind to receptor molecules or epitopes of interest or gene products that modify peptides or RNA in a desired fashion. The random, pseudorandom, and defined sequence framework peptides are produced from libraries of peptide library members that comprise displayed peptides or displayed single-chain antibodies attached to a polynucleotide template from which the displayed peptide was synthesized. The mode of attachment may vary according to the specific embodiment of the invention selected, and can include encapsulation in a phage particle or incorporation in a cell.

A method of affinity enrichment allows a very large library of peptides and single-chain antibodies to be screened and the polynucleotide sequence encoding the desired peptide(s) or single-chain antibodies to be selected. The polynucleotide can then be isolated and shuffled to recombine combinatorially the amino acid sequence of the selected peptide(s) (or predetermined portions thereof) or single-chain antibodies (or just VHI, VLI or CDR portions thereof). Using these methods, one can identify a peptide or single-chain antibody as having a desired binding affinity for a molecule and can exploit the process of shuffling to converge rapidly to a desired high-affinity peptide or scfv. The peptide or antibody can then be synthesized in bulk by conventional means for any suitable use (e.g., as a therapeutic or diagnostic agent).

A significant advantage of the present invention is that no prior information regarding an expected ligand structure is required to isolate peptide ligands or antibodies of interest. The peptide identified can have biological activity, which is meant to include at least specific binding affinity for a selected receptor molecule and, in some instances, will further include the ability to block the binding of other compounds, to stimulate or inhibit metabolic pathways, to act as a signal or messenger, to stimulate or inhibit cellular activity, and the like.

The present invention also provides a method for shuffling a pool of polynucleotide sequences selected by affinity screening a library of polysomes displaying nascent peptides (including single-chain antibodies) for library members which bind to a predetermined receptor (e.g., a mammalian proteinaceous receptor such as, for example, a peptidergic hormone receptor, a cell surface receptor, an intracellular protein which binds to other protein(s) to form intracellular protein complexes such as hetero-dimers and the like) or epitope (e.g., an immobilized protein, glycoprotein, oligosaccharide, and the like).

Polynucleotide sequences selected in a first selection round (typically by affinity selection for binding to a receptor (e.g., a ligand)) by any of these methods are pooled and the pool(s) is/are shuffled by in vitro and/or in vivo recombination to produce a shuffled pool comprising a population of recombined selected polynucleotide sequences. The recombined selected polynucleotide sequences are subjected to at least one subsequent selection round. The polynucleotide sequences selected in the subsequent selection round(s) can be used directly, sequenced, and/or subjected to one or more additional rounds of shuffling and subsequent selection. Selected sequences can also be back-crossed with polynucleotide sequences encoding neutral sequences (i.e., having insubstantial functional effect on binding), such as for example by back-crossing with a wild-type or naturally-occurring sequence substantially identical to a selected sequence to produce native-like functional peptides, which may be less immunogenic. Generally, during back-crossing subsequent selection is applied to retain the property of binding to the predetermined receptor (ligand).

Prior to or concomitant with the shuffling of selected sequences, the sequences can be mutagenized. In one embodiment, selected library members are cloned in a prokaryotic vector (e.g., plasmid, phagemid, or bacteriophage) wherein a collection of individual colonies (or plaques) representing discrete library members are produced. Individual selected library members can then be manipulated (e.g., by site-directed mutagenesis, cassette mutagenesis, chemical mutagenesis, PCR mutagenesis, and the like) to generate a collection of library members representing a kernal of sequence diversity based on the sequence of the selected library member. The sequence of an individual selected library member or pool can be manipulated to incorporate random mutation, pseudorandom mutation, defined kernal mutation (i.e., comprising variant and invariant residue positions and/or comprising variant residue positions which can comprise a residue selected from a defined subset of amino acid residues), codon-based mutation, and the like, either segmentally or over the entire length of the individual selected library member sequence. The mutagenized selected library members are then shuffled by in vitro and/or in vivo recombinatorial shuffling as disclosed herein.

The invention also provides peptide libraries comprising a plurality of individual library members of the invention, wherein (1) each individual library member of said plurality comprises a sequence produced by shuffling of a pool of selected sequences, and (2) each individual library member comprises a variable peptide segment sequence or single-chain antibody segment sequence which is distinct from the variable peptide segment sequences or single-chain antibody sequences of other individual library members in said plurality (although some library members may be present in more than one copy per library due to uneven amplification, stochastic probability, or the like).

The invention also provides a product-by-process, wherein selected polynucleotide sequences having (or encoding a peptide having) a predetermined binding specificity are formed by the process of: (1) screening a displayed peptide or displayed single-chain antibody library against a predetermined receptor (e.g., ligand) or epitope (e.g., antigen macromolecule) and identifying and/or enriching library members which bind to the predetermined receptor or epitope to produce a pool of selected library members, (2) shuffling by recombination the selected library members (or amplified or cloned copies thereof) which binds the predetermined epitope and has been thereby isolated and/or enriched from the library to generate a shuffled library, and (3) screening the shuffled library against the predetermined receptor (e.g., ligand) or epitope (e.g., antigen macromolecule) and identifying and/or enriching shuffled library members which bind to the predetermined receptor or epitope to produce a pool of selected shuffled library members.

Antibody Display and Screening Methods

The present method can be used to shuffle, by in vitro and/or in vivo recombination by any of the disclosed methods, and in any combination, polynucleotide sequences selected by antibody display methods, wherein an associated polynucleotide encodes a displayed antibody which is screened for a phenotype (e.g., for affinity for binding a predetermined antigen (ligand).

Various molecular genetic approaches have been devised to capture the vast immunological repertoire represented by the extremely large number of distinct variable regions which can be present in immunoglobulin chains. The naturally-occurring germ line immunoglobulin heavy chain locus is composed of separate tandem arrays of variable segment genes located upstream of a tandem array of diversity segment genes, which are themselves located upstream of a tandem array of joining (i) region genes, which are located upstream of the constant region genes. During B lymphocyte development, V-D-J rearrangement occurs wherein a heavy chain variable region gene (VH) is formed by rearrangement to form a fused D segment followed by rearrangement with a V segment to form a V-D-J joined product gene which, if productively rearranged, encodes a functional variable region (VH) of a heavy chain. Similarly, light chain loci rearrange one of several V segments with one of several J segments to form a gene encoding the variable region (VL) of a light chain.

The vast repertoire of variable regions possible in immunoglobulins derives in part from the numerous combinatorial possibilities of joining V and i segments (and, in the case of heavy chain loci, D segments) during rearrangement in B cell development. Additional sequence diversity in the heavy chain variable regions arises from non-uniform rearrangements of the D segments during V-D-J joining and from N region addition. Further, antigen-selection of specific B cell clones selects for higher affinity variants having non-germline mutations in one or both of the heavy and light chain variable regions; a phenomenon referred to as "affinity maturation" or "affinity sharpening". Typically, these "affinity sharpening" mutations cluster in specific areas of the variable region, most commonly in the complementarity-determining regions (CDRs).

In order to overcome many of the limitations in producing and identifying high-affinity immunoglobulins through antigen-stimulated β cell development (i.e., immunization), various prokaryotic expression systems have been developed that can be manipulated to produce combinatorial antibody libraries which may be screened for high-affinity antibodies to specific antigens. Recent advances in the expression of antibodies in *Escherichia coli* and bacteriophage systems (see, "Alternative Peptide Display Methods", infra) have raised the possibility that virtually any specificity can be obtained by either cloning antibody genes from characterized hybridomas or by de novo selection using antibody gene libraries (e.g., from Ig CDNA).

Combinatorial libraries of antibodies have been generated in bacteriophage lambda expression systems which may be screened as bacteriophage plaques or as colonies of lysogens (Huse et al. (1989) *Science* 246: 1275; Caton and Koprowski (1990) *Proc. Natl. Acad. Sci. (U.S.A.)* 87: 6450; Mullinax et al (1990) *Proc. Natl. Acad. Sci. (U.S.A.)* 87: 8095; Persson et al. (1991) *Proc. Natl. Acad. Sci. (T.J.S.A.)* 88: 2432). Various embodiments of bacteriophage antibody display libraries and lambda phage expression libraries have been described (Kang et al. (1991) *Proc. Natl. Acad. Sci. (U.S.A.)* 88: 4363; Clackson et al. (1991) *Nature* 352: 624; McCafferty et al. (1990) *Nature* 348: 552; Burton et al. (1991) *Proc. Natl- Acad. Sci. (U.S.A.)* 88: 10134; Hoogenboom et al. (1991) *Nucleic Acids Res.* 19: 4133; Chang et al. (1991) *J. Immunol.* 147: 3610; Breitling et al. (1991) *Gene* 104: 147; Marks et al. (1991) *J. Mol. Biol.* 222@: 581; Barbas et al. (1992) *Proc. Natl. Acad. Sci. (U.S.A.)* 89: 4457; Hawkins and Winter (1992) *J. Immunol.* 22: 867; Marks et al. (1992) *Biotechnology* 10: 779; Marks et al. (1992) *J. Biol. Chem.* 267: 16007; Lowman et al (1991) *Biochemistry* 30: 10832; Lerner et al. (1992) *Science.* 258: 1313, incorporated herein by reference). Typically, a bacteriophage antibody display library is screened with a receptor (e.g., polypeptide, carbohydrate, glycoprotein, nucleic acid) that is immobilized (e.g., by covalent linkage to a chromatography resin to enrich for reactive phage by affinity chromatography) and/or labeled (e.g., to screen plaque or colony lifts).

One particularly advantageous approach has been the use of so-called single-chain fragment variable (scfv) libraries (Marks et al. (1992) *Biotechnology* 10: 779; Winter G and Milstein C (1991) *Nature* 349: 293; Clackson et al. (1991) op. cit.; Marks et al. (1991) *J. Mol. Biol.* 222: 581; Chaudhary et al. (1990) *Proc. Natl. Acad. Sci. (USA)* 87: 1066; Chiswell et al. (1992) *TIBTECH* 10: 80; McCafferty et al. (1990) op.cit.; and Huston et al- (1988) *Proc. Natl. Acad. Sci. (USA)* 85: 5879). Various embodiments of scfv libraries displayed on bacteriophage coat proteins have been described.

Beginning in 1988, single-chain analogues of Fv fragments and their fusion proteins have been reliably generated by antibody engineering methods. The first step generally involves obtaining the genes encoding VH and VL domains with desired binding properties; these V genes may be isolated from a specific hybridoma cell line, selected from a combinatorial V-gene library, or made by V gene synthesis. The single-chain Fv is formed by connecting the component V genes with an oligonucleotide that encodes an appropriately designed linker peptide, such as (Gly-Gly-Gly-Gly-Ser)3 or equivalent linker peptide(s). The linker bridges the C-terminus of the first V region and N-terminus of the second, ordered as either VH-linker-VL or VL-linker-VH' In principle, the scfv binding site can faithfully replicate both the affinity and specificity of its parent antibody combining site.

Thus, scfv fragments are comprised of VH and VL domains linked into a single polypeptide chain by a flexible linker peptide. After the scfv genes are assembled, they are cloned into a phagemid and expressed at the tip of the M13 phage (or similar filamentous bacteriophage) as fusion proteins with the bacteriophage PIII (gene 3) coat protein. Enriching for phage expressing an antibody of interest is accomplished by panning the recombinant phage displaying a population scfv for binding to a predetermined epitope (e.g., target antigen, receptor).

The linked polynucleotide of a library member provides the basis for replication of the library member after a screening or selection procedure, and also provides the basis for the determination, by nucleotide sequencing, of the identity of the displayed peptide sequence or VH and VL amino acid sequence. The displayed peptide (s) or single-chain antibody (e. g., scfv) and/or its VH and VL domains or their CDRs can be cloned and expressed in a suitable expression system. often polynucleotides encoding the isolated VH and VL domains will be ligated to polynucleotides encoding constant regions (CH and CL) to form polynucleotides encoding complete antibodies (e.g., chimeric or fully-human), antibody fragments, and the like. Often polynucleotides encoding the isolated CDRs will be grafted into polynucleotides encoding a suitable variable region framework (and optionally constant regions) to form polynucleotides encoding complete antibodies (e.g., humanized or fully-human), antibody fragments, and the like. Antibodies can be used to isolate preparative quantities of the antigen by immunoaffinity chromatography. Various other uses of such antibodies are to diagnose and/or stage disease (e.g., neoplasia) and for therapeutic application to treat disease, such as for example: neoplasia, autoimmune disease, AIDS, cardiovascular disease, infections, and the like.

Various methods have been reported for increasing the combinatorial diversity of a scfv library to broaden the repertoire of binding species (idiotype spectrum) The use of PCR has permitted the variable regions to be rapidly cloned either from a specific hybridoma source or as a gene library from non-immunized cells, affording combinatorial diversity in the assortment of VH and VL cassettes which can be combined. Furthermore, the VH and VL cassettes can themselves be diversified, such as by random, pseudorandom, or directed mutagenesis. Typically, VH and VL cassettes are diversified in or near the complementarity-determining regions (CDRS), often the third CDR, CDR3. Enzymatic inverse PCR mutagenesis has been shown to be a simple and reliable method for constructing relatively large libraries of scfv site-directed hybrids (Stemmer et al. (1993) *Biotechniques* 14: 256), as has error-prone PCR and chemical mutagenesis (Deng et al. (1994) *J. Biol. Chem.* 269: 953 3). Riechmann et al. (1993) *Biochemistry* 32: 8848 showed semi-rational design of an antibody scfv fragment using site-directed randomization by degenerate oligonucleotide PCR and subsequent phage display of the resultant scfv hybrids. Barbas et al. (1992) on.cit. attempted to circumvent the problem of limited repertoire sizes resulting from using biased variable region sequences by randomizing the sequence in a synthetic CDR region of a human tetanus toxoid-binding Fab.

CDR randomization has the potential to create approximately $1 \times 10^{20}$ CDRs for the heavy chain CDR3 alone, and a roughly similar number of variants of the heavy chain CDR1 and CDR2, and light chain CDR1–3 variants. Taken individually or together, the combination possibilities of CDR randomization of heavy and/or light chains requires generating a prohibitive number of bacteriophage clones to produce a clone library representing all possible combinations, the vast majority of which will be non-binding. Generation of such large numbers of primary transformants is not feasible with current transformation technology and bacteriophage display systems. For example, Barbas et al. (1992) op.cit. only generated $5 \times 10^7$ transformants, which represents only a tiny fraction of the potential diversity of a library of thoroughly randomized CDRS.

Despite these substantial limitations, bacteriophage. display of scfv have already yielded a variety of useful antibodies and antibody fusion proteins. A bispecific single chain antibody has been shown to mediate efficient tumor cell lysis (Gruber et al. (1994) *J. Immunol.* 152: 5368). Intracellular expression of an anti-Rev scfv has been shown to inhibit HIV-1 virus replication in vitro (Duan et al. (1994) *Proc. Natl. Acad. Sci. (USA)* 91: 5075), and intracellular expression of an anti-p21rar, scfv has been shown to inhibit meiotic maturation of *Xenopus oocytes* (Biocca et al. (1993) *Biochem. Bioshys. Res. Commun.* 197: 422. Recombinant scfv which can be used to diagnose HIV infection have also been reported, demonstrating the diagnostic utility of scfv (Lilley et al. (1994) *J. Immunol. Meth.* 171: 211). Fusion proteins wherein an scFv is linked to a second polypeptide, such as a toxin or fibrinolytic activator protein, have also been reported (Holvost et al. (1992) *Eur. J. Biochess.* 210: 945; Nicholls et al. (1993) *J. Biol. Chem.* 268: 5302).

If it were possible to generate scfv libraries having broader antibody diversity and overcoming many of the limitations of conventional CDR mutagenesis and randomization methods which can cover only a very tiny fraction of the potential sequence combinations, the number and quality of scfv antibodies suitable for therapeutic and diagnostic use could be vastly improved. To address this, the in vitro and in vivo shuffling methods of the invention are used to recombine CDRs which have been obtained (typically via PCR amplification or cloning) from nucleic acids obtained from selected displayed antibodies. Such displayed antibodies can be displayed on cells, on bacteriophage particles, on polysomes, or any suitable antibody display system wherein the antibody is associated with its encoding nucleic acid(s). In a variation, the CDRs are initially obtained from MRNA (or CDNA) from antibody-producing cells (e.g., plasma cells/splenocytes from an immunized wild-type mouse, a human, or a transgenic mouse capable of making a human antibody as in W092/03918, W093/12227, and W094/25585), including hybridomas derived therefrom.

Polynucleotide sequences selected in a first selection round (typically by affinity selection for displayed antibody binding to an antigen (e.g., a ligand) by any of these methods are pooled and the pool(s) is/are shuffled by in vitro and/or in vivo recombination, especially shuffling of CDRs (typically shuffling heavy chain CDRs with other heavy chain CDRs and light chain CDRs with other light chain CDRS) to produce a shuffled pool comprising a population of recombined selected polynucleotide sequences. The recombined selected polynucleotide sequences are expressed in a selection format as a displayed antibody and subjected to at least one subsequent selection round. The polynucleotide sequences selected in the subsequent selection round(s) can be used directly, sequenced, and/or subjected to one or more additional rounds of shuffling and subsequent selection until an antibody of the desired binding affinity is obtained. Selected sequences can also be back-crossed with polynucleotide sequences encoding neutral antibody framework sequences (i.e., having insubstantial functional effect on antigen binding), such as for example by back-crossing with a human variable region framework to produce human-like sequence antibodies. Generally, during back-crossing subsequent selection is applied to retain the property of binding to the predetermined antigen.

Alternatively, or in combination with the noted variations, the valency of the target epitope may be varied to control the average binding affinity of selected scfv library members. The target epitope can be bound to a surface or substrate at varying densities, such as by including a competitor epitope, by dilution, or by other method known to those in the art. A high density (valency) of predetermined epitope can be used to enrich for scfv library members which have relatively low affinity, whereas a low density (valency) can preferentially enrich for higher affinity scfv library members.

For generating diverse variable segments, a collection of synthetic oligonucleotides encoding random, pseudorandom, or a defined sequence kernal set of peptide sequences can be inserted by ligation into a predetermined site (e.g., a CDR). Similarly, the sequence diversity of one or more CDRs of the single-chain antibody cassette(s) can be expanded by mutating the CDR(s) with site-directed mutagenesis, CDR-replacement, and the like. The resultant DNA molecules can be propagated in a host for cloning and amplification prior to shuffling, or can be used directly (i.e., may avoid loss of diversity which may occur upon propagation in a host cell) and the selected library members subsequently shuffled.

Displayed peptide/polynucleotide complexes (library members) which encode a variable segment peptide sequence of interest or a single-chain antibody of interest are selected from the library by an affinity enrichment technique. This is accomplished by means of a immobilized macromolecule or epitope specific for the peptide sequence of interest, such as a receptor, other macromolecule, or other epitope species. Repeating the affinity selection procedure provides an enrichment of library members encoding the desired sequences, which may then be isolated for pooling and shuffling, for sequencing, and/or for further propagation and affinity enrichment.

The library members without the desired specificity are removed by washing. The degree and stringency of washing required will be determined for each peptide sequence or single-chain antibody of interest and the immobilized predetermined macromolecule or epitope. A certain degree of control can be exerted over the binding characteristics of the nascent peptide/DNA complexes recovered by adjusting the conditions of the binding incubation and the subsequent washing. The temperature, pH, ionic strength, divalent cations concentration, and the volume and duration of the washing will select for nascent peptide/DNA complexes within particular ranges of affinity for the immobilized macromolecule. Selection based on slow dissociation rate, which is usually predictive of high affinity, is often the most practical route. This may be done either by continued incubation in the presence of a saturating amount of free predetermined macromolecule, or by increasing the volume, number, and length of the washes. In each case, the rebinding of dissociated nascent peptide/DNA or peptide/RNA complex is prevented, and with increasing time, nascent peptide/DNA or peptide/RNA complexes of higher and higher affinity are recovered.

Additional modifications of the binding and washing procedures may be applied to find peptides with special characteristics. The affinities of some peptides are dependent on ionic strength or cation concentration. This is a useful characteristic for peptides that will be used in affinity purification of various proteins when gentle conditions for removing the protein from the peptides are required.

One variation involves the use of multiple binding targets (multiple epitope species, multiple receptor species), such that a scfv library can be simultaneously screened for a multiplicity of scfv which have different binding specificities. Given that the size of a scfv library often limits the diversity of potential scfv sequences, it is typically desirable to us scfv libraries of as large a size as possible. The time and economic considerations of generating a number of very large polysome scFv-display libraries can become prohibitive. To avoid this substantial problem, multiple predetermined epitope species (receptor species) can be concomitantly screened in a single library, or sequential screening against a number of epitope species can be used. In one variation, multiple target epitope species, each encoded on a separate bead (or subset of beads), can be mixed and incubated with a polysome-display scfv library under suitable binding conditions. The collection of beads, comprising multiple epitope species, can then be used to isolate, by affinity selection, scfv library members. Generally, subsequent affinity screening rounds can include the same mixture of beads, subsets thereof, or beads containing only one or two individual epitope species. This approach affords efficient screening, and is compatible with laboratory automation, batch processing, and high throughput screening methods.

A variety of techniques can be used in the present invention to diversify a peptide library or single-chain antibody library, or to diversify, prior to or concomitant with shuffling, around variable segment peptides found in early rounds of panning to have sufficient binding activity to the predetermined macromolecule or epitope. In one approach, the positive selected peptide/polynucleotide complexes (those identified in an early round of affinity enrichment) are sequenced to determine the identity of the active peptides. Oligonucleotides are then synthesized based on these active peptide sequences, employing a low level of all bases incorporated at each step to produce slight variations of the primary oligonucleotide sequences. This mixture of (slightly) degenerate oligonucleotides is then cloned into the variable segment sequences at the appropriate locations. This method produces systematic, controlled variations of the starting peptide sequences, which can then be shuffled. It requires, however, that individual positive nascent peptide/polynucleotide complexes be sequenced before mutagenesis, and thus is useful for expanding the diversity of small numbers of recovered complexes and selecting variants having higher binding affinity and/or higher binding specificity. In a variation, mutagenic PCR amplification of positive selected peptide/polynucleotide complexes (especially of the variable region sequences, the amplification products of which are shuffled in vitro and/or in vivo and one or more additional rounds of screening is done prior to sequencing. The same general approach can be employed with single-chain antibodies in order to expand the diversity and enhance the binding affinity/specificity, typically by diversifying CDRs or adjacent framework regions prior to or concomitant with shuffling. If desired, shuffling reactions can be spiked with mutagenic oligonucleotides capable of in vitro recombination with the selected library members can be included. Thus, mixtures of synthetic oligonucleotides and PCR produced polynucleotides (synthesized by error-prone or high-fidelity methods) can be added to the in vitro shuffling mix and be incorporated into resulting shuffled library members (shufflants).

The present invention of shuffling enables the generation of a vast library of CDR-variant single-chain antibodies. One way to generate such antibodies is to insert synthetic CDRs into the single-chain antibody and/or CDR randomization prior to or concomitant with shuffling. The sequences of the synthetic CDR cassettes are selected by referring to known sequence data of human CDR and are selected in the discretion of the practitioner according to the following guidelines: synthetic CDRs will have at least 40 percent positional sequence identity to known CDR sequences, and preferably will have at least 50 to 70 percent positional sequence identity to known CDR sequences. For example, a collection of synthetic CDR sequences can be generated by synthesizing a collection of oligonucleotide sequences on the basis of naturally-occurring human CDR sequences listed in Kabat et al. (1991) op. cit. ; the pool (s) of synthetic CDR sequences are calculated to encode CDR peptide sequences having at least 40 percent sequence identity to at least one known naturally-occurring human CDR sequence. Alternatively, a collection of naturally-occurring CDR sequences may be compared to generate consensus sequences so that amino acids used at a residue position frequently (i.e., in at least 5 percent of known CDR sequences) are incorporated into the synthetic CDRs at the corresponding position(s). Typically, several (e.g., 3 to about 50) known CDR sequences are compared and observed natural sequence variations between the known CDRs are tabulated, and a collection of oligonucleotides encoding CDR peptide sequences encompassing all or most permutations of the observed natural sequence variations is synthesized. For example but not for limitation, if a collection of human VH CDR sequences have carboxy-terminal amino acids which are either Tyr, Val, Phe, or Asp, then the pool(s) of synthetic CDR oligonucleotide sequences are designed to allow the carboxy-terminal CDR residue to be any of these amino acids. In some embodiments, residues other than those which naturally-occur at a residue position in the collection of CDR sequences are incorporated: conservative amino acid substitutions are frequently incorporated and up to 5 residue positions may be varied to incorporate non-conservative amino acid substitutions as compared to known naturally-occurring CDR sequences. Such CDR sequences can be used in primary library members (prior to first round screening) and/or can be used to spike in vitro shuffling reactions of selected library member sequences. Construction of such pools of defined and/or degenerate sequences will be readily accomplished by those of ordinary skill in the art.

The collection of synthetic CDR sequences comprises at least one member that is not known to be a naturally-occurring CDR sequence. It is within the discretion of the practitioner to include or not include a portion of random or pseudorandom sequence corresponding to N region addition in the heavy chain CDR; the N region sequence ranges from 1 nucleotide to about 4 nucleotides occurring at V-D and D-J junctions. A collection of synthetic heavy chain CDR sequences comprises at least about 100 unique CDR sequences, typically at least about 1,000 unique CDR sequences, preferably at least about 10,000 unique CDR sequences, frequently more than 50,000 unique CDR sequences; however, usually not more than about $1 \times 10^6$ unique CDR sequences are included in the collection, although occasionally $1 \times 10^7$ to $1 \times 10^8$ unique CDR sequences are present, especially if conservative amino acid substitutions are permitted at positions where the conservative amino acid substituent is not present or is rare (i.e., less than 0.1 percent) in that position in naturally-occurring human CDRS. In general, the number of unique CDR sequences included in a library should not exceed the expected number of primary transformants in the library by more than a factor of 10. Such single-chain antibodies generally bind of about at least $1 \times 10$ m-, preferably with an affinity of about at least $5 \times 10^7$ M-1, more preferably with an affinity of at least $1 \times 10^8$ M-1 to $1 \times 10^9$ M-1 or more, sometimes up to $1 \times 10^{10}$ M-1 or more. Frequently, the predetermined antigen is a human protein, such as for example a human cell surface antigen (e. g., CD4, CD8, IL-2 receptor, EGF receptor, PDGF receptor), other human biological macromolecule (e.g., thrombomodulin, protein C, carbohydrate antigen, sialyl Lewis antigen, Lselectin), or nonhuman disease associated macromolecule (e.g., bacterial LPS, virion capsid protein or envelope glycoprotein) and the like.

High affinity single-chain antibodies of the desired specificity can be engineered and expressed in a variety of systems. For example, scfv have been produced in plants (Firek et al. (1993) *Plant Mol. Biol.* 23: 861) and can be readily made in prokaryotic systems (Owens R J and Young R J (1994) *J. Immunol. Meth.* 168: 149; Johnson S and Bird R E (1991) *Methods Enzvmol*203: 88). Furthermore, the single-chain antibodies can be used as a basis for constructing whole antibodies or various fragments thereof (Kettleborough et al. (1994) *Eur. J. Immunol.* 24: 952). The variable region encoding sequence may be isolated (e.g., by PCR amplification or subcloning) and spliced to a sequence encoding a desired human constant region to encode a human sequence antibody more suitable for human therapeutic uses where immunogenicity is preferably minimized. The polynucleotide(s) having the resultant fully human encoding sequence(s) can be expressed in a host cell (e.g., from an expression vector in a mammalian cell) and purified for pharmaceutical formulation.

The DNA expression constructs will typically include an expression control DNA sequence operably linked to the coding sequences, including naturally-associated or heterologous promoter regions. Preferably, the expression control sequences will be eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the mutant' "engineered" antibodies.

As stated previously, the DNA sequences will be expressed in hosts after the sequences have been operably linked to an expression control sequence (i.e., positioned to ensure the transcription and translation of the structural gene). These expression vectors are typically replicable in the host organisms either as episomes or as an integral part of the host chromosomal DNA. Commonly, expression vectors will contain selection markers, e.g., tetracycline or neomycin, to permit detection of those cells transformed with the desired DNA sequences (see, e.g., U.S. Pat. No. 4,704,362, which is incorporated herein by reference).

In addition to eukaryotic microorganisms such as yeast, mammalian tissue cell culture may also be used to produce the polypeptides of the present invention (see, Winnacker, "From Genes to Clones," VCH Publishers, N.i., N.Y. (1987), which is incorporated herein by reference). Eukaryotic cells are actually preferred, because a number of suitable host cell lines capable of secreting intact immunoglobulins have been developed in the art, and include the CHO cell lines, various COS cell lines, HeLa cells, and myeloma cell lines, but preferably transformed Bcells or hybridomas. Expression vectors for these cells can include expression control sequences, such as an origin of replication, a promoter, an enhancer (Queen et al. (1986) Immunol. Rev. 89: 49), and necessary processing information sites, such as ribosome binding sites, RNA splice sites, polyadenylation sites, and transcriptional terminator sequences. Preferred expression control sequences are promoters derived from immunoglobulin genes, cytomegalovirus, SV40, Adenovirus, Bovine Papilloma Virus, and the like.

Eukaryotic DNA transcription can be increased by inserting an enhancer sequence into the vector. Enhancers are cis-acting sequences of between 10 to 300 bp that increase transcription by a promoter. Enhancers can effectively increase transcription when either 51 or 31 to the transcription unit. They are also effective if located within an intron or within the coding sequence itself. Typically, viral enhancers are used, including SV40 enhancers, cytomegalovirus enhancers, polyoma enhancers, and adenovirus enhancers.

Enhancer sequences from mammalian systems are also commonly used, such as the mouse immunoglobulin heavy chain enhancer.

Mammalian expression vector systems will also typically include a selectable marker gene. Examples of suitable markers include, the dihydrofolate reductase gene (DHFR), the thymidine kinase gene (TK), or prokaryotic genes conferring drug resistance. The first two marker genes prefer the use of mutant cell lines that lack the ability to grow without the addition of thymidine to the growth medium. Transformed cells can then be identified by their ability to grow on non-supplemented media. Examples of prokaryotic drug resistance genes useful as markers include genes conferring resistance to G418, mycophenolic acid and hygromycin.

The vectors containing the DNA segments of interest can be transferred into the host cell by well-known methods, depending on the type of cellular host. For example, calcium chloride transfection is commonly utilized for prokaryotic cells, whereas calcium phosphate treatment. lipofection, or electroporation may be used for other cellular hosts. Other methods used to transform mammalian cells include the use of Polybrene, protoplast fusion, liposomes, electroporation, and micro-injection (see. generally, Sambrook et al., supra).

Once expressed, the antibodies, individual mutated immunoglobulin chains, mutated antibody fragments, and other immunoglobulin polypeptides of the invention can be purified according to standard procedures of the art, including ammonium sulfate precipitation, fraction column chromatography, gel electrophoresis and the like (see, generally, Scopes, R., *Protein* Purification, Springer-Verlag, N.Y. (1982)). once purified, partially or to homogeneity as desired, the polypeptides may then be used therapeutically or in developing and performing assay procedures, immunofluorescent stainings, and the like (see, generally, *Immunological Methods,* Vols. I and II, Eds. Lefkovits and Pernis, Academic Press, New York, N.Y. (1979 and 1981)).

The antibodies generated by the method of the present invention can be used for diagnosis and therapy. By way of illustration and not limitation, they can be used to treat cancer, autoimmune diseases, or viral infections. For treatment of cancer, the antibodies will typically bind to an antigen expressed preferentially on cancer cells, such as erbB-2, CEA, CD33, and many other antigens and binding members well known to those skilled in the art.

Yeast Two-Hybrid Screening Assays

Shuffling can also be used to recombinatorially diversify a pool of selected library members obtained by screening a two-hybrid screening system to identify library members which bind a predetermined polypeptide sequence. The selected library members are pooled and shuffled by in vitro and/or in vivo recombination. The shuffled pool can then be screened in a yeast two hybrid system to select library members which bind said predetermined polypeptide sequence (e. g., and SH2 domain) or which bind an alternate predetermined polypeptide sequence (e.g., an SH2 domain from another protein species).

An approach to identifying polypeptide sequences which bind to a predetermined polypeptide sequence has been to use a so-called "two-hybrid" system wherein the predetermined polypeptide sequence is present in a fusion protein (Chien et al. (1991) *Proc. Natl. Acad. Sci.* (*USA*) 88: 9578). This approach identifies protein-protein interactions in vivo through reconstitution of a transcriptional activator (Fields S and Song 0 (1989) *Nature* 340: 245), the yeast Gal4 transcription protein. Typically, the method is based on the properties of the yeast Gal4 protein, which consists of separable domains responsible for DNA-binding and transcriptional activation. Polynucleotides encoding two hybrid proteins, one consisting of the yeast Gal4 DNA-binding domain fused to a polypeptide sequence of a known protein and the other consisting of the Gal4 activation domain fused to a polypeptide sequence of a second protein, are constructed and introduced into a yeast host cell. Intermolecular binding between the two fusion proteins reconstitutes the Gal4 DNA-binding domain with the Gal4 activation domain, which leads to the transcriptional activation of a reporter gene (e.g., lacz, HIS3) which is operably linked to a Gal4 binding site. Typically, the two-hybrid method is used to identify novel polypeptide sequences which interact with a known protein (Silver S C and Hunt S W (1993) *Mol. Biol. Rep.* 17: 155; Durfee et al. (1993) *Genes Devel.* 7: 555; Yang et al. (1992) *Science* 257: 680; Luban et al. (1993) *Cell* 73: 1067; Hardy et al(1992) *Genes Devel.* 6: 801; Bartel et al. (1993) *Biotechniques* 14: 920; and Vojtek et al. (1993) *Cell* 74: 205). However, variations of the two-hybrid method have been used to identify mutations of a known protein that affect its binding to a second known protein (Li B and Fields S (1993) *FASEB J.* 7: 957; Lalo et al. (1993) *Proc. Natl. Acad. Sci. (USA)* 90: 5524; Jackson et al(1993) *Mol. Cell. Biol.* 13: 2899; and Madura et al. (1993) *J. Biol- Chem.* 268: 12046). Two-hybrid systems have also been used to identify interacting structural domains of two known proteins (Bardwell et al. (1993) *med. Microbial.* 8: 1177; Chakrabarty et al. (1992) *J. Biol. Chem.* 267: 17498; Staudinger et al. (1993) *J. Biol. Chem.* 268: 4608; and Milne G T. and Weaver D T (1993) *Genes Devel.* 7: 1755) or domains responsible for oligomerization of a single protein (Iwabuchi et al. (1993) *Oncogene* 8; 1693; Bogerd et al. (1993) *J. Virol.* 67: 5030). Variations of two-hybrid systems have been used to study the in vivo activity of a proteolytic enzyme (Dasmahapatra et al. (1992) *Proc. Natl. Acad. Sci. (USA)* 89: 4159). Alternatively, an *E. coli* /BCCP interactive screening system (Germino et al. (1993) *Proc. Natl. Acad. Sci. (U.S.A.)* 90: 933; Guarente L (1993) *Proc. Natl. Acad. Sci. (U.S.A.)* 90: 1639) can be used to identify interacting protein sequences (i.e., protein sequences which heterodimerize or form higher order heteromultimers). Sequences selected by a two-hybrid system can be pooled and shuffled and introduced into a two-hybrid system for one or more subsequent rounds of screening to identify polypeptide sequences which bind to the hybrid containing the predetermined binding sequence. The sequences thus identified can be compared to identify consensus sequence(s) and consensus sequence kernals.

In general, standard techniques of recombination DNA technology are described in various publications, e.g. Sambrook et al., 1989, Molecular Cloning: A Laboratory Manual, Cold Spring Harbor Laboratory; Ausubel et al., 1987, Current Protocols in Molecular Biology, vols. 1 and 2 and supplements, and Berger and Kimmel, *Methods in Enzymology, Volume 152, Guide to Molecular Cloning Technicrues* (1987), Academic Press, Inc., San Diego, Calif., each of which is incorporated herein in their entirety by reference. Polynucleotide modifying enzymes were used according to the manufacturers recommendations. Oligonucleotides were synthesized on an Applied Biosystems Inc. Model 394 DNA synthesizer using ABI chemicals. If desired, PCR amplimers for amplifying a predetermined DNA sequence may be selected at the discretion of the practitioner.

One microgram samples of template DNA are obtained and treated with U.V. light to cause the formation of dimers, including TT dimers, particularly purine dimers. U.V. exposure is limited so that only a few photoproducts are generated per gene on the template DNA sample. Multiple samples are treated with U.V. light for varying periods of time to obtain template DNA samples with varying numbers of dimers from U.V. exposure.

A random priming kit which utilizes a non-proofreading polymease (for example, Prime-It II Random Primer Labeling kit by Stratagene Cloning Systems) is utilized to generate different size polynucleotides by priming at random sites on templates which are prepared by U.V. light (as described above) and extending along the templates. The priming protocols such as described in the Prime-It II Random Primer Labeling kit may be utilized to extend the primers. The dimers formed by U.V. exposure serve as a roadblock for the extension by the non-proofreading polymerase. Thus, a pool of random size polynucleotides is present after extension with the random primers is finished.

The present invention is further directed to a method for generating a selected mutant polynucleotide sequence (or a population of selected polynucleotide sequences) typically in the form of amplified and/or cloned polynucleotides, whereby the selected polynucleotide sequences(s) possess at least one desired phenotypic characteristic (e.g., encodes a polypeptide, promotes transcription of linked polynucleotides, binds a protein, and the like) which can be selected for. One method for identifying hybrid polypeptides that possess a desired structure or functional property, such as binding to a predetermined biological macromolecule (e.g., a receptor), involves the screening of a large library of polypeptides for individual library members which possess the desired structure or functional property conferred by the amino acid sequence of the polypeptide.

In one embodiment, the present invention provides a method for generating libraries of displayed polypeptides or displayed antibodies suitable for affinity interaction screening or phenotypic screening. The method comprises (1) obtaining a first plurality of selected library members comprising a displayed polypeptide or displayed antibody and an associated polynucleotide encoding said displayed polypeptide or displayed antibody, and obtaining said associated polynucleotides or copies thereof wherein said associated polynucleotides comprise a region of substantially identical sequences, optimally introducing mutations into said polynucleotides or copies, (2) pooling the polynucleotides or copies, (3) producing smaller or shorter polynucleotides by interrupting a random or particularized priming and synthesis process or an amplification process, and (4) performing amplification, preferably PCR amplification, and optionally mutagenesis to homologously recombine the newly synthesized polynucleotides.

It is a particularly preferred object of the invention to provide a process for producing hybrid polynucleotides which express a useful hybrid polypeptide by a series of steps comprising:

(a) producing polynucleotides by interrupting a polynucleotide amplification or synthesis process with a means for blocking or interrupting the amplification or synthesis process and thus providing a plurality of smaller or shorter polynucleotides due to the replication of the polynucleotide being in various stages of completion;

(b) adding to the resultant population of single- or double-stranded polynucleotides one or more single- or double-stranded oligonucleotides, wherein said added oligonucleotides comprise an area of identity in an area of heterology to one or more of the single- or double-stranded polynucleotides of the population;

(c) denaturing the resulting single- or double-stranded oligonucleotides to produce a mixture of single-stranded polynucleotides, optionally separating the shorter or smaller polynucleotides into pools of polynucleotides having various lengths and further optionally subjecting said polynucleotides to a PCR procedure to amplify one or more oligonucleotides comprised by at least one of said polynucleotide pools;

(d) incubating a plurality of said polynucleotides or at least one pool of said polynucleotides with a polymerase under conditions which result in annealing of said single-stranded polynucleotides at regions of identity between the single-stranded polynucleotides and thus forming of a mutagenized double-stranded polynucleotide chain;

(e) optionally repeating steps (c) and (d);

(f) expressing at least one hybrid polypeptide from said polynucleotide chain, or chains; and (g) screening said at least one hybrid polypeptide for a useful activity.

In a preferred aspect of the invention, the means for blocking or interrupting the amplification or synthesis process is by utilization of uv light, DNA adducts, DNA binding proteins.

In one embodiment of the invention, the DNA adducts, or polynucleotides comprising the DNA adducts, are removed from the polynucleotides or polynucleotide pool, such as by a process including heating the solution comprising the DNA fragments prior to further processing.

Having thus disclosed exemplary embodiments of the present invention, it should be noted by those skilled in the art that the disclosures are exemplary only and that various other alternatives, adaptations and modifications may be made within the scope of the present invention. Accordingly, the present invention is not limited to the specific embodiments as illustrated herein.

Without further elaboration, it is believed that one skilled in the art can, using the preceding description, utilize the present invention to its fullest extent. The following examples are to be considered illustrative and thus are not limiting of the remainder of the disclosure in any way whatsoever.

EXAMPLE 1

Generation of Random Size Polynucleotides Using U.V. Induced Photoproducts

One microgram samples of template DNA are obtained and treated with U.V. light to cause the formation of dimers, including TT dimers, particularly purine dimers. U.V. exposure is limited so that only a few photoproducts are generated per gene on the template DNA sample. Multiple samples are treated with U.V. light for varying periods of time to obtain template DNA samples with varying numbers of dimers from U.V. exposure.

A random priming kit which utilizes a non-proofreading polymease (for example, Prime-It II Random Primer Labeling kit by Stratagene Cloning Systems) is utilized to generate different size polynucleotides by priming at random sites on templates which are prepared by U.V. light (as described above) and extending along the templates. The priming protocols such as described in the Prime-It II Random Primer Labeling kit may be utilized to extend the primers. The dimers formed by U.V. exposure serve as a roadblock for the extension by the non-proofreading polymerase. Thus, a pool of random size polynucleotides is present after extension with the random primers is finished.

EXAMPLE 2

Isolation of Random Size Polynucleotides

Polynucleotides of interest which are generated according to Example 1 are are gel isolated on a 1.5% agarose gel. Polynucleotides in the 100–300 bp range are cut out of the gel and 3 volumes of 6 M NaI is added to the gel slice. The mixture is incubated at 50° C. for 10 minutes and 10 $\mu$l of glass milk (Bio 101) is added. The mixture is spun for 1 minute and the supernatant is decanted. The pellet is washed with 500 $\mu$l of Column Wash (Column Wash is 50% ethanol, 10 mM Tris-HCl pH 7.5, 100 mM NaCl and 2.5 mM EDTA) and spin for 1 minute, after which the supernatant is decanted. The washing, spinning and decanting steps are then repeated. The glass milk pellet is resuspended in 20 $\mu$l of $H_2O$ and spun for 1 minute. DNA remains in the aqueous phase.

EXAMPLE 3

Shuffling of Isolated Random Size 100–300 bp Polynucleotides

The 100–300 bp polynucleotides obtained in Example 2 are recombined in an annealing mixture (0.2 mM each dNTP, 2.2 mM $MgCl_2$, 50 mM KCl, 10 mM Tris-HCl ph 8.8, 0.1% Triton X-100, 0.3$\mu$; Taq DNA polymerase, 50 $\mu$l total volume) without adding primers. A Robocycler by Stratagene was used for the annealing step with the following program: 95° C. for 30 seconds, 25–50 cycles of [95° C. for 30 seconds, 50–60° C. (preferably 58° C.) for 30 seconds, and 72° C. for 30 seconds] and 5 minutes at 72° C. Thus, the 100–300 bp polynucleotides combine to yield double-stranded polynucleotides having a longer sequence. After separating out the reassembled double-stranded polynucleotides and denaturing them to form single stranded polynucleotides, the cycling is optionally again repeated with some samples utilizing the single strands as template and primer DNA and other samples utilizing random primers in addition to the single strands.

EXAMPLE 4

Screening of Polypeptides from Shuffled Polynucleotides

The polynucleotides of Example 3 are separated and polypeptides are expressed therefrom. The original template DNA is utilized as a comparative control by obtaining comparative polypeptides therefrom. The polypeptides obtained from the shuffled polynucleotides of Example 3 are screened for the activity of the polypeptides obtained from the original template and compared with the activity levels of the control. The shuffled polynucleotides coding for interesting polypeptides discovered during screening are compared further for secondary desirable traits. Some shuffled polynucleotides corresponding to less interesting screened polypeptides are subjected to reshuffling.

What is claimed is:

1. A method for producing hybrid polynucleotides comprising:

creating mutations in one or more samples of nucleic acid sequences;

optionally screening for desired characteristics within the samples of mutagenized nucleic acid sequences; and transforming each of a plurality of host cells with one or more nucleic acid sequences having said desired characteristics, wherein said one or more nucleic acid sequences include at least a first polynucleotide that shares at least one region of partial sequence homology with a second polynucleotide in the host cell;

wherein said partial sequence homology promotes reassortment processes which result in sequence reorganization; thereby producing said hybrid polynucleotides.

2. The method of claim 1, wherein at least one of the hybrid polynucleotides encodes a biologically active hybrid polypeptide.

3. The method of claim 1, wherein the at least first polynucleotide or second polynucleotide encodes a biologically active polypeptide.

4. The method of claim 1, wherein the at least first polynucleotide or second polynucleotide comprises one or more operons, or portions thereof.

5. The method of claim 4, wherein the operon, or portions thereof, encodes a complete or partial metabolic pathway.

6. The method of claim 1, wherein the plurality of host cells are selected from the group consisting of a bacterium, fungus, plant cell, insect cell and animal cells.

7. The method of claim 1, further comprising growing the plurality of host cells under conditions which allow for the expression of a biologically active hybrid polypeptide encoded by the hybrid polynucleotide.

8. The method of claim 1, wherein the first and second polynucleotides are different and are present in a vector.

9. The method of claim 1, wherein the first and second polynucleotides are different and are present in the same vector.

10. The method of claim 1, wherein the first and second polynucleotides are in different vectors.

11. The method of claim 8, wherein the vector is selected from the group consisting of phage, plasmids, phagemids, cosmids, fosmids, viral vectors and artificial chromosomes.

12. The method of claim 1, wherein the sequence reorganization is by reductive reassortment.

13. The method of claim 1, wherein the first and second polynucleotides are from uncultivated microorganisms derived from an environmental sample.

14. The method of claim 13, wherein the uncultivated organisms comprise a mixture of terrestrial microorganisms or marine microorganisms, or a mixture of terrestrial microorganisms and marine microorganisms.

15. The method of claim 14, wherein the microorganisms in the environmental sample are extremophiles.

16. The method of claim 1, wherein the mutations are introduced by a method selected from the group consisting of error-prone PCR, oligonucleotide-directed mutagenesis, chemical mutagens, ultraviolet light, x-rays and a combination thereof.

17. The method of claim 1, wherein the sample of nucleic acids is in a cell.

18. The method of claim 16, wherein the cell is an *E.coli*.

19. The method of claim 16, wherein the nucleic acids are chromosomal.

20. The method of claim 16, wherein the nucleic acids are episomal.

21. The method of claim 1, wherein at least one of the nucleic acid sequences is a wild-type sequence and the processes include back-crossing.

22. The method of claim 1, wherein the plurality of host cells are contained in a library.

23. The method of claim 1, wherein the mutations are created in the samples of nucleic acid sequences in vivo within a cell, and wherein the cells are grown and selected based on the desired characteristics.

24. The method of claim 1, wherein at least one of nucleic acid sequences introduced into the host cell contains consecutive regions of homology.

* * * * *